United States Patent
Samsonov et al.

(10) Patent No.: US 11,746,345 B2
(45) Date of Patent: Sep. 5, 2023

(54) METHOD FOR PRODUCING AN L-AMINO ACID USING A BACTERIUM OF THE FAMILY ENTEROBACTERIACEAE HAVING AN ATTENUATED EXPRESSION OF A GSHA GENE

(71) Applicant: AJINOMOTO CO., INC., Tokyo (JP)

(72) Inventors: Valery Vasilievich Samsonov, Moscow (RU); Natalia Sergeevna Eremina, Moscow (RU); Natalia Viktorovna Stoynova, Moscow (RU)

(73) Assignee: AJINOMOTO CO., INC., Tokyo (JP)

( * ) Notice: Subject to any disclaimer, the term of this patent is extended or adjusted under 35 U.S.C. 154(b) by 434 days.

(21) Appl. No.: 15/165,606

(22) Filed: May 26, 2016

(65) Prior Publication Data

US 2016/0348089 A1 Dec. 1, 2016

(30) Foreign Application Priority Data

May 28, 2015 (RU) .......................... RU2015120052

(51) Int. Cl.
| | |
|---|---|
| *C12N 9/00* | (2006.01) |
| *C12P 13/08* | (2006.01) |
| *C12P 13/04* | (2006.01) |
| *C12N 15/52* | (2006.01) |
| *C12P 13/06* | (2006.01) |
| *C12P 13/10* | (2006.01) |
| *C12P 13/12* | (2006.01) |
| *C12P 13/14* | (2006.01) |
| *C12P 13/22* | (2006.01) |
| *C12P 13/24* | (2006.01) |

(52) U.S. Cl.
CPC .............. *C12N 9/93* (2013.01); *C12N 15/52* (2013.01); *C12P 13/04* (2013.01); *C12P 13/06* (2013.01); *C12P 13/08* (2013.01); *C12P 13/10* (2013.01); *C12P 13/12* (2013.01); *C12P 13/14* (2013.01); *C12P 13/222* (2013.01); *C12P 13/227* (2013.01); *C12P 13/24* (2013.01); *C12Y 603/02002* (2013.01)

(58) Field of Classification Search
None
See application file for complete search history.

(56) References Cited

U.S. PATENT DOCUMENTS

| | | | |
|---|---|---|---|
| 4,278,765 A | 7/1981 | Debabov et al. | |
| 4,346,170 A | 8/1982 | Sano et al. | |
| 5,120,654 A * | 6/1992 | Marquardt ........... | C12N 9/1096 435/108 |
| 5,661,012 A | 8/1997 | Sano et al. | |
| 5,965,391 A | 10/1999 | Reinscheid et al. | |
| 5,998,178 A | 12/1999 | Hashiguchi et al. | |
| 6,040,160 A | 3/2000 | Kojima et al. | |
| 8,460,903 B2 | 6/2013 | Savrasova et al. | |
| 8,679,798 B2 | 3/2014 | Yampolskaya et al. | |
| 8,852,897 B2 | 10/2014 | Savrasova et al. | |
| 9,175,319 B2 | 11/2015 | Stoynova et al. | |
| 9,279,137 B2 | 3/2016 | Sycheva et al. | |
| 9,873,898 B2 * | 1/2018 | Kuvaeva ............. | C12P 13/10 |
| 2006/0216796 A1 | 9/2006 | Hashiguchi et al. | |
| 2007/0004001 A1 | 1/2007 | Calhoun et al. | |
| 2007/0026505 A1 * | 2/2007 | Madden ............. | C07K 14/24 435/106 |
| 2011/0212496 A1 | 9/2011 | Takikawa et al. | |
| 2012/0237986 A1 | 9/2012 | Ziyatdinov et al. | |
| 2013/0078682 A1 | 3/2013 | Filippov et al. | |
| 2015/0017693 A1 | 1/2015 | Sycheva et al. | |

FOREIGN PATENT DOCUMENTS

| | | | |
|---|---|---|---|
| CN | 1680547 A | | 10/2005 |
| CN | 101831397 | | 9/2010 |
| CN | 101831397 B | * | 1/2012 |
| CN | 103003437 A | | 3/2013 |
| EP | 0685555 | | 12/1995 |
| EP | 2336347 A1 | | 6/2011 |
| WO | WO95/16042 | | 6/1995 |
| WO | WO96/15246 | | 5/1996 |
| WO | WO02/29080 A2 | | 4/2002 |
| WO | WO2006/138322 A2 | | 12/2006 |
| WO | WO2006/138322 A3 | | 12/2006 |

OTHER PUBLICATIONS

Translation of Chinese patent CN 101831397 B, Jan. 25, 2012.*
Uniprot, Accession No. B6ICC5, 2013, www.uniprot.org.*
Park et al., Metabolic engineering of *Escherichia coli* for the production of L-valine based on transcriptome analysis and in silico gene knockout simulation, Proc. Natl. Acad. Sci. USA, 2007, 104, 7797-7802.*
Umbarge et al., Amino acid biosynthesis and its regulation, Ann. Rev. Biochem., 1978, 47, 533-660.*
Apontowell, P., et al., "Glutathione Biosynthesis in *Escherichia coli* K12 Properties of the Enzymes and Regulation," Biochimica et Biophysica Acta 1975;399:1-9.
Database UniProt [online] May 27, 2015, "RecName: Full= Glutamate—cysteine ligase", retrieved from EBI accession No. UniProt: M9E1R3 Database accession No. M9E1R3.
Calhoun, K. A., et al., "Total amino acid stabilization during cell-free protein synthesis reactions," J. Biotechnol. 2006;123:193-203.
Extended European Search Report for European Patent App. No. 16171303.7 (dated Sep. 30, 2016).
Database Epodoc [Online] Oct. 13, 2010 European Patent Office, The Hague, NL; "*Escherichia coli* and method for preparing L-cysteine by using same", Database accession No. CN-201010136361-A.

(Continued)

*Primary Examiner* — Todd M Epstein
(74) *Attorney, Agent, or Firm* — Cermak Nakajima & McGowan LLP; Shelly Guest Cermak

(57) ABSTRACT

The present invention provides a method for producing an L-amino acid such as a branched-chain L-amino acid by fermentation using a bacterium of the family Enterobacteriaceae, particularly a bacterium belonging to the genus *Escherichia*, which has been modified to attenuate expression of the gshA gene.

11 Claims, No Drawings

Specification includes a Sequence Listing.

(56) References Cited

OTHER PUBLICATIONS

First Office Action for Chinese Patent App. No. 201610366024.8 (dated Jul. 30, 2020) with English language translation thereof.
NCBI Reference Sequence: WP_000611804.1, Multispecies: glutamate-cysteine ligase [Enterobacteriaceae], None, Genbank; Apr. 27, 2015.
U.S. Appl. No. 15/082,274, Kuvaeva et al., filed Mar. 28, 2016.

\* cited by examiner

SEQUENCE LISTING

<160> NUMBER OF SEQ ID NOS: 9

<210> SEQ ID NO 1
<211> LENGTH: 1557
<212> TYPE: DNA
<213> ORGANISM: Escherichia coli

<400> SEQUENCE: 1

| | | | | | |
|---|---|---|---|---|---|
| ttgatcccgg | acgtatcaca | ggcgctggcc | tggctggaaa | acatcctca | ggcgttaaag | 60 |
| gggatacagc | gtgggctgga | gcgcgaaact | ttgcgtgtta | atgctgatgg | cacactggca | 120 |
| acaacaggtc | atcctgaagc | attaggttcc | gcactgacgc | acaaatggat | tactaccgat | 180 |
| tttgcggaag | cattgctgga | attcattaca | ccagtggatg | gtgatattga | acatatgctg | 240 |
| acctttatgc | gcgatctgca | tcgttatacg | gcgcgcaata | tgggcgatga | gcggatgtgg | 300 |
| ccgttaagta | tgccatgcta | catcgcagaa | ggtcaggaca | tcgaactggc | acagtacggc | 360 |
| acttctaaca | ccggacgctt | taaaacgctg | tatcgtgaag | gctgaaaaa | tcgctacggc | 420 |
| gcgctgatgc | aaaccatttc | cggcgtgcac | tacaatttct | ctttgccaat | ggcattctgg | 480 |
| caagcgaagt | gcggtgatat | ctcgggcgct | gatgccaaag | agaaaatttc | tgcgggctat | 540 |
| ttccgcgtta | tccgcaatta | ctatcgtttc | ggttgggtca | ttccttatct | gtttggtgca | 600 |
| tctccggcga | tttgttcttc | tttcctgcaa | ggaaaaccaa | cgtcgctgcc | gtttgagaaa | 660 |
| accgagtgcg | gtatgtatta | cctgccgtat | gcgacctctc | ttcgtttgag | cgatctcggc | 720 |
| tataccaata | aatcgcaaag | caatcttggt | attaccttca | acgatcttta | cgagtacgta | 780 |
| gcgggcctta | acaggcaat | caaaacgcca | tcggaagagt | acgcgaagat | tggtattgag | 840 |
| aaagacggta | agaggctgca | aatcaacagc | aacgtgttgc | agattgaaaa | cgaactgtac | 900 |
| gcgccgattc | gtccaaaacg | cgttacccgc | agcggcgagt | cgccttctga | tgcgctgtta | 960 |
| cgtggcggca | ttgaatatat | tgaagtgcgt | tcgctggaca | tcaacccgtt | ctcgccgatt | 1020 |
| ggtgtagatg | aacagcaggt | gcgattcctc | gacctgttta | tggtctggtg | tgcgctggct | 1080 |
| gatgcaccgg | aaatgagcag | tagcgaactt | gcctgtacac | gcgttaactg | gaaccgggtg | 1140 |
| atcctcgaag | gtcgcaaacc | gggtctgacg | ctgggtatcg | gctgcgaaac | cgcacagttc | 1200 |
| ccgttaccgc | aggtgggtaa | agatctgttc | cgcgatctga | aacgcgtcgc | gcaaacgctg | 1260 |
| gatagtatta | acggcggcga | agcgtatcag | aaagtgtgtg | atgaactggt | tgcctgcttc | 1320 |
| gataatcccg | atctgacttt | ctctgcccgt | atcttaaggt | ctatgattga | tactggtatt | 1380 |
| ggcggaacag | gcaaagcatt | tgcagaagcc | taccgtaatc | tgctgcgtga | agagccgctg | 1440 |
| gaaattctgc | gcgaagagga | ttttgtagcc | gagcgcgagg | cgtctgaacg | ccgtcagcag | 1500 |
| gaaatggaag | ccgctgatac | cgaaccgttt | gcggtgtggc | tggaaaaaca | cgcctga | 1557 |

<210> SEQ ID NO 2
<211> LENGTH: 518
<212> TYPE: PRT
<213> ORGANISM: Escherichia coli

<400> SEQUENCE: 2

Met Ile Pro Asp Val Ser Gln Ala Leu Ala Trp Leu Glu Lys His Pro
1               5                   10                  15

Gln Ala Leu Lys Gly Ile Gln Arg Gly Leu Glu Arg Glu Thr Leu Arg
            20                  25                  30

Val Asn Ala Asp Gly Thr Leu Ala Thr Thr Gly His Pro Glu Ala Leu
        35                  40                  45

```
Gly Ser Ala Leu Thr His Lys Trp Ile Thr Thr Asp Phe Ala Glu Ala
 50                  55                  60

Leu Leu Glu Phe Ile Thr Pro Val Asp Gly Asp Ile Glu His Met Leu
 65                  70                  75                  80

Thr Phe Met Arg Asp Leu His Arg Tyr Thr Ala Arg Asn Met Gly Asp
                 85                  90                  95

Glu Arg Met Trp Pro Leu Ser Met Pro Cys Tyr Ile Ala Glu Gly Gln
                100                 105                 110

Asp Ile Glu Leu Ala Gln Tyr Gly Thr Ser Asn Thr Gly Arg Phe Lys
                115                 120                 125

Thr Leu Tyr Arg Glu Gly Leu Lys Asn Arg Tyr Gly Ala Leu Met Gln
130                 135                 140

Thr Ile Ser Gly Val His Tyr Asn Phe Ser Leu Pro Met Ala Phe Trp
145                 150                 155                 160

Gln Ala Lys Cys Gly Asp Ile Ser Gly Ala Asp Ala Lys Glu Lys Ile
                165                 170                 175

Ser Ala Gly Tyr Phe Arg Val Ile Arg Asn Tyr Tyr Arg Phe Gly Trp
                180                 185                 190

Val Ile Pro Tyr Leu Phe Gly Ala Ser Pro Ala Ile Cys Ser Ser Phe
                195                 200                 205

Leu Gln Gly Lys Pro Thr Ser Leu Pro Phe Glu Lys Thr Glu Cys Gly
                210                 215                 220

Met Tyr Tyr Leu Pro Tyr Ala Thr Ser Leu Arg Leu Ser Asp Leu Gly
225                 230                 235                 240

Tyr Thr Asn Lys Ser Gln Ser Asn Leu Gly Ile Thr Phe Asn Asp Leu
                245                 250                 255

Tyr Glu Tyr Val Ala Gly Leu Lys Gln Ala Ile Lys Thr Pro Ser Glu
                260                 265                 270

Glu Tyr Ala Lys Ile Gly Ile Glu Lys Asp Gly Lys Arg Leu Gln Ile
                275                 280                 285

Asn Ser Asn Val Leu Gln Ile Glu Asn Glu Leu Tyr Ala Pro Ile Arg
290                 295                 300

Pro Lys Arg Val Thr Arg Ser Gly Glu Ser Pro Ser Asp Ala Leu Leu
305                 310                 315                 320

Arg Gly Gly Ile Glu Tyr Ile Glu Val Arg Ser Leu Asp Ile Asn Pro
                325                 330                 335

Phe Ser Pro Ile Gly Val Asp Glu Gln Gln Val Arg Phe Leu Asp Leu
                340                 345                 350

Phe Met Val Trp Cys Ala Leu Ala Asp Ala Pro Glu Met Ser Ser Ser
                355                 360                 365

Glu Leu Ala Cys Thr Arg Val Asn Trp Asn Arg Val Ile Leu Glu Gly
                370                 375                 380

Arg Lys Pro Gly Leu Thr Leu Gly Ile Gly Cys Glu Thr Ala Gln Phe
385                 390                 395                 400

Pro Leu Pro Gln Val Gly Lys Asp Leu Phe Arg Asp Leu Lys Arg Val
                405                 410                 415

Ala Gln Thr Leu Asp Ser Ile Asn Gly Gly Glu Ala Tyr Gln Lys Val
                420                 425                 430

Cys Asp Glu Leu Val Ala Cys Phe Asp Asn Pro Asp Leu Thr Phe Ser
                435                 440                 445

Ala Arg Ile Leu Arg Ser Met Ile Asp Thr Gly Ile Gly Gly Thr Gly
450                 455                 460
```

```
Lys Ala Phe Ala Glu Ala Tyr Arg Asn Leu Leu Arg Glu Glu Pro Leu
465                 470                 475                 480

Glu Ile Leu Arg Glu Glu Asp Phe Val Ala Glu Arg Glu Ala Ser Glu
            485                 490                 495

Arg Arg Gln Gln Glu Met Glu Ala Ala Asp Thr Glu Pro Phe Ala Val
        500                 505                 510

Trp Leu Glu Lys His Ala
        515

<210> SEQ ID NO 3
<211> LENGTH: 63
<212> TYPE: DNA
<213> ORGANISM: Artificial Sequence
<220> FEATURE:
<223> OTHER INFORMATION: Primer P1

<400> SEQUENCE: 3
ccctgaattc agagatgaaa ttttggccac tcacgtgaag cctgcttttt tatactaagt    60
tgg                                                                 63

<210> SEQ ID NO 4
<211> LENGTH: 64
<212> TYPE: DNA
<213> ORGANISM: Artificial Sequence
<220> FEATURE:
<223> OTHER INFORMATION: Primer P2

<400> SEQUENCE: 4
tgcacatatg gtcaccatta cagttatgct aattaacgct caagttagta taaaaaagct    60
gaac                                                                64

<210> SEQ ID NO 5
<211> LENGTH: 1378
<212> TYPE: DNA
<213> ORGANISM: Artificial Sequence
<220> FEATURE:
<223> OTHER INFORMATION: PCR-product 1

<400> SEQUENCE: 5
ccctgaattc agagatgaaa ttttggccac tcacgtgaag cctgcttttt tatactaagt    60
tggcattata aaaagcattg cttatcaatt tgttgcaacg aacaggtcac tatcagtcaa   120
aataaaatca ttatttgatt tcgtcgagtt acgccccgcc ctgccactca tcgcagtact   180
gttgtaattc attaagcatt ctgccgacat ggaagccatc acagacggca tgatgaacct   240
gaatcgccag cggcatcagc accttgtcgc cttgcgtata atatttgccc atggtgaaaa   300
cgggggcgaa gaagttgtcc atattggcca cgtttaaatc aaaactggtg aaactcaccc   360
agggattggc tgagacgaaa aacatattct caataaaccc tttagggaaa taggccaggt   420
tttcaccgta acacgccaca tcttgcgaat atatgtgtag aaactgccgg aaatcgtcgt   480
ggtattcact ccagagcgat gaaaacgttt cagtttgctc atggaaaacg gtgtaacaag   540
ggtgaacact atcccatatc accagctcac cgtctttcat tgccatacgg aattccggat   600
gagcattcat caggcgggca agaatgtgaa taaaggccgg ataaaacttg tgcttatttt   660
tctttacggt ctttaaaaag gccgtaatat ccagctgaac ggtctggtta taggtacatt   720
gagcaactga ctgaaatgcc tcaaaatgtt ctttacgatg ccattgggat atatcaacgg   780
tggtatatcc agtgattttt ttctccattt tagcttcctt agctcctgaa aatctcgata   840
```

```
actcaaaaaa tacgcccggt agtgatctta tttcattatg gtgaaagttg gaacctctta    900
cgtgccgatc aacgtctcat tttcgccaaa agttggccca gggcttcccg gtatcaacag    960
ggacaccagg atttatttat tctgcgaagt gatcttccgt cacaggtatt tattcggcgc   1020
aaagtgcgtc gggtgatgct gccaacttac tgatttagtg tatgatggtg ttttttgaggt 1080 gctccagtgg cttctgtttc tatcagctgt ccctcctgtt cagctactga cggggtggtg   1140
cgtaacggca aaagcaccgc cggacatcag ctgcagtctg ttacaggtca ctaataccat   1200
ctaagtagtt gattcatagt gactgcatat gttgtgtttt acagtattat gtagtctgtt   1260
ttttatgcaa aatctaattt aatatattga tatttatatc attttacgtt tctcgttcag   1320 ctttttttata ctaacttgag cgttaattag cataactgta atggtgacca tatgtgca    1378
```

<210> SEQ ID NO 6
<211> LENGTH: 20
<212> TYPE: DNA
<213> ORGANISM: Artificial Sequence
<220> FEATURE:
<223> OTHER INFORMATION: Primer P3

<400> SEQUENCE: 6
agcgttacgc tatgttgcag                                                 20

<210> SEQ ID NO 7
<211> LENGTH: 20
<212> TYPE: DNA
<213> ORGANISM: Artificial Sequence
<220> FEATURE:
<223> OTHER INFORMATION: Primer P4

<400> SEQUENCE: 7
ctttccaggc atcagcaaca                                                 20

<210> SEQ ID NO 8
<211> LENGTH: 2155
<212> TYPE: DNA
<213> ORGANISM: Artificial Sequence
<220> FEATURE:
<223> OTHER INFORMATION: PCR-product 2

<400> SEQUENCE: 8

```
ctttccaggc atcagcaaca cgctgctcat ctggcgtacc aatcagactc atataaaaac     60
cggtgcggca gcccattggc gagatatcga taatctctac accattaccg ttaagatggt    120
tacgcataaa accagcaaac aggtgctcca gggtatggga ccctcttttct ggcatcactt   180 ctttgttcgg cacgcagaag cgcagatcga acacggtgat tgcgtcgcca tgcggggtgt    240
tcattgtttt cgccacccga actgcaggcg cttccatccg ggtatgatcg actgtgaagc    300
tatctaacaa cggcatttag ccacctccgg taattttttt aaaaattttc tgaactcttt    360
cttcccaggc gagtctgagt atatgaaaga cgcgcatttg ttatcatcat ccctgaattc    420
agagatgaaa ttttggccac tcacgagtgg ccttttctct ttctgtcagg cgtgtttttc    480
cagccacacc gcaaacggtt cggtatcagc ggcttccatt tcctgctgac ggcgttcaga    540
cgcctcgcgc tcggctacaa aatcctcttc gcgcagaatt tccagcggct cttcacgcag    600
cagattacgg taggcttctg caaatgcttt gcctgttccg ccaataccag tatcaatcat    660
agaccttaag atacgggcag agaaagtcag atcgggatta tcgaagcagg caaccagttc    720
atcacacact ttctgatacg cttcgccgcc gttaatacta tccagcgttt gcgcgacgcg    780
tttcagatcg cggaacagat cttttacccac ctgcggtaac gggaactgtg cggtttcgca    840
```

```
gccgataccc agcgtcagac ccggtttgcg accttcgagg atcacccggt tccagttaac      900
gcgtgtacag gcaagttcgc tactgctcat ttccggtgca tcagccagcg cacaccagac      960
cataaacagg tcgaggaatc gcacctgctg ttcatctaca ccaatcggcg agaacgggtt     1020
gatgtccagc gaacgcactt caatatattc aatgccgcca cgtaacagcg catcagaagg     1080
cgactcgccg ctgcgggtaa cgcgttttgg acgaatcggc gcgtacagtt cgttttcaat     1140
ctgcaacacg ttgctgttga tttgcagcct cttaccgtct ttctcaatac caatcttcgc     1200
gtactcttcc gatggcgttt tgattgcctg tttaaggccc gctacgtact cgtaaagatc     1260
gttgaaggta ataccaagat tgctttgcga tttattggta tagccgagat cgctcaaacg     1320
aagagaggtc gcatacggca ggtaatacat accgcactcg gttttctcaa acggcagcga     1380
cgttggtttt ccttgcagga agaagaacaa atcgccgga gatgcaccaa acagataagg      1440
aatgacccaa ccgaaacgat agtaattgcg gataacgcgg aaatagcccg cagaaatttt     1500
ctctttggca tcagcgcccg agatatcacc gcacttcgct tgccagaatg ccattggcaa     1560
agagaaattg tagtgcacgc cggaaatggt ttgcatcagc gcgccgtagc gattttttcag    1620 cccttcacga tacagcgttt taaagcgtcc ggtgttagaa gtgccgtact gtgccagttc     1680
gatgtcctga ccttctgcga tgtagcatgg catacttaac ggccacatcc gctcatcgcc     1740
catattgcgc ccgtataac gatgcagatc gcgcataaag gtcagcatat gttcaatatc      1800
accatccact ggtgtaatga attccagcaa tgcttccgca aaatcggtag taatccattt     1860
gtgcgtcagt gcggaaccta atgcttcagg atgacctgtt gttgccagtg tgccatcagc     1920
attaacacgc aaagtttcgc gctccagccc acgctgtatc ccctttaacg cctgaggatg     1980
tttttccagc caggccagcg cctgtgatac gtccgggatc aaattgacct cccgcctgtc     2040
aaaatcgttt taattagcat aactgtaatg gtgaccatat gtgcaggcct acaattagtg     2100
ccaccacatc atgccctgaa cggtcgctgc tgcaactgca acatagcgta acgct          2155
```

<210> SEQ ID NO 9
<211> LENGTH: 1858
<212> TYPE: DNA
<213> ORGANISM: Artificial Sequence
<220> FEATURE:
<223> OTHER INFORMATION: PCR-product 3

<400> SEQUENCE: 9

```
ctttccaggc atcagcaaca cgctgctcat ctggcgtacc aatcagactc atataaaaac       60
cggtgcggca gcccattggc gagatatcga taatctctac accattaccg ttaagatggt      120
tacgcataaa accagcaaac aggtgctcca gggtatggat ccctctttct ggcatcactt      180
ctttgttcgg cacgcagaag cgcagatcga acacggtgat tgcgtcgcca tgcgggtgt       240 tcattgtttt cgccacccga actgcaggcg cttccatccg ggtatgatcg actgtgaagc      300
tatctaacaa cggcatttag ccacctccgg taatttttt aaaaattttc tgaactcttt       360
cttcccaggc gagtctgagt atatgaaaga cgcgcatttg ttatcatcat ccctgaattc      420
agagatgaaa ttttggccac tcacgtgaag cctgcttttt tatactaagt tggcattata     480
aaaagcattg cttatcaatt tgttgcaacg aacaggtcac tatcagtcaa aataaaatca     540
ttatttgatt tcgtcgagtt acgccccgcc ctgccactca tcgcagtact gttgtaattc     600
attaagcatt ctgccgacat ggaagccatc acagacggca tgatgaacct gaatcgccag    660
cggcatcagc accttgtcgc cttgcgtata atatttgccc atggtgaaaa cggggggcgaa     720
```

```
gaagttgtcc atattggcca cgtttaaatc aaaactggtg aaactcaccc agggattggc    780
tgagacgaaa aacatattct caataaaccc tttagggaaa taggccaggt tttcaccgta    840
acacgccaca tcttgcgaat atatgtgtag aaactgccgg aaatcgtcgt ggtattcact    900
ccagagcgat gaaaacgttt cagtttgctc atggaaaacg gtgtaacaag ggtgaacact    960
atcccatatc accagctcac cgtctttcat tgccatacgg aattccggat gagcattcat   1020
caggcgggca agaatgtgaa taaaggccgg ataaaacttg tgcttatttt tctttacggt   1080
ctttaaaaag gccgtaatat ccagctgaac ggtctggtta taggtacatt gagcaactga   1140
ctgaaatgcc tcaaaatgtt ctttacgatg ccattgggat atatcaacgg tggtatatcc   1200
agtgattttt ttctccattt tagcttcctt agctcctgaa aatctcgata actcaaaaaa   1260
tacgcccggt agtgatctta tttcattatg gtgaaagttg gaacctctta cgtgccgatc   1320
aacgtctcat tttcgccaaa agttggccca gggcttcccg gtatcaacag ggacaccagg   1380
atttatttat tctgcgaagt gatcttccgt cacaggtatt tattcggcgc aaagtgcgtc   1440
gggtgatgct gccaacttac tgatttagtg tatgatggtg tttttgaggt gctccagtgg   1500
cttctgtttc tatcagctgt ccctcctgtt cagctactga cggggtggtg cgtaacggca   1560
aaagcaccgc cggacatcag ctgcagtctg ttacaggtca ctaataccat ctaagtagtt   1620
gattcatagt gactgcatat gttgtgtttt acagtattat gtagtctgtt ttttatgcaa   1680
aatctaattt aatatattga tatttatatc attttacgtt tctcgttcag cttttttata   1740
ctaacttgag cgttaattag cataactgta atggtgacca tatgtgcagg cctacaatta   1800
gtgccaccac atcatgccct gaacggtcgc tgctgcaact gcaacatagc gtaacgct    1858
```

METHOD FOR PRODUCING AN L-AMINO ACID USING A BACTERIUM OF THE FAMILY ENTEROBACTERIACEAE HAVING AN ATTENUATED EXPRESSION OF A GSHA GENE

This application claims priority under 35 U.S.C. § 119 to Russian Patent Application No. 2015120052, filed May 28, 2015, the entirety of which is incorporated by reference herein. Also, the Sequence Listing filed electronically herewith is hereby incorporated by reference (File name: 2016-05-26T_US-547_Seq_List; File size: 15 KB; Date recorded: May 26, 2016).

BACKGROUND OF THE INVENTION

Field of the Invention

The present invention relates generally to the microbiological industry, and specifically to a method for producing L-amino acids by fermentation of a bacterium of the family Enterobacteriaceae that has been modified to attenuate expression of the gshA gene, so that production of L-amino acids is enhanced.

Brief Description of the Related Art

Conventionally, L-amino acids are industrially produced by fermentation methods utilizing strains of microorganisms obtained from natural sources, or mutants thereof. Typically, the microorganisms are modified to enhance production yields of L-amino acids.

Many techniques to enhance L-amino acid production yields have been reported, including transformation of microorganisms with recombinant DNA (see, for example, U.S. Pat. No. 4,278,765 A) and alteration of expression regulatory regions such as promoters, leader sequences, and/or attenuators, or others known to the person skilled in the art (see, for example, US20060216796 A1 and WO9615246 A1). Other techniques for enhancing production yields include increasing the activities of enzymes involved in amino acid biosynthesis and/or desensitizing the target enzymes to the feedback inhibition by the resulting L-amino acid (see, for example, WO9516042 A1, EP0685555 A1 or U.S. Pat. Nos. 4,346,170 A, 5,661,012 A, and 6,040,160 A).

Another method for enhancing L-amino acids production yields is to attenuate expression of a gene or several genes that is/are involved in degradation of the target L-amino acid, genes which divert the precursors of the target L-amino acid from the L-amino acid biosynthetic pathway, genes involved in the redistribution of the carbon, nitrogen, and phosphate fluxes, and genes encoding toxins, etc.

The gshA gene encodes γ-glutamate-cysteine ligase which catalyzes the first of two steps in the pathway for the biosynthesis of glutathione from L-glutamate. The enzyme is feedback-inhibited by glutathione (Apontoweil P. and Berends W., Glutathione biosynthesis in *Escherichia coli* K 12. Properties of the enzymes and regulation, *Biochim. Biophys. Acta*, 1975, 399(1):1-9). An *Escherichia coli* BL21 (DE3) strain having the increased activity of serine acetyl transferase (SAT) and the metC, tnaA, gshA and dfp genes deleted was utilized in a method for L-cysteine production by fermentation of the bacterium (CN101831397 A).

However, no data has been previously reported that describes the effect from attenuating expression of the gshA gene on production of L-amino acids by fermentation of an L-amino acid-producing bacterium of the family Enterobacteriaceae.

SUMMARY OF THE INVENTION

An aspect of the present invention is to provide a method for producing L-amino acids such as L-alanine, L-arginine, L-asparagine, L-aspartic acid, L-citrulline, L-cysteine, L-glutamic acid, L-glutamine, glycine, L-histidine, L-isoleucine, L-leucine, L-lysine, L-methionine, L-ornithine, L-phenylalanine, L-proline, L-serine, L-threonine, L-tryptophan, L-tyrosine, and L-valine using a bacterium belonging to the family Enterobacteriaceae, which can belong to the genus *Escherichia* and, more specifically, to the species *Escherichia coli* (*E. coli*), and which has been modified to attenuate expression of the gshA gene.

This aim was achieved by the finding that attenuation of expression of the gshA gene on the chromosome of an L-amino acid-producing bacterium belonging to the family Enterobacteriaceae, which can belong to the genus *Escherichia* and, more specifically, to the species *E. coli*, confers on the bacterium a higher productivity of L-amino acids, more specifically, branched-chain L-amino acids and, in particular, but is not limited to, L-valine. Furthermore, the production yield of L-amino acids, such as, for example, branched-chain L-amino acids, including L-valine, by fermentation of the modified bacterium of the family Enterobacteriaceae can be increased. The gshA gene can be attenuated, for example, by inactivation of expression of the gshA gene on the chromosome of a bacterium belonging to the family Enterobacteriaceae, which can belong to the genus *Escherichia* and, more specifically, to the species *E. coli*. These findings have resulted in the following non-limiting aspects of the present invention.

It is one aspect of the present invention to provide a method for producing an L-amino acid comprising:

(i) cultivating an L-amino acid-producing bacterium of the family Enterobacteriaceae in a culture medium to produce the L-amino acid in the culture medium, the bacterium, or both; and (ii) collecting the L-amino acid from the culture medium, the bacterium, or both, wherein the bacterium has been modified to attenuate expression of a gshA gene.

It is a further aspect of the present invention to provide the method as described above, wherein the bacterium belongs to the genus *Escherichia*.

It is a further aspect of the present invention to provide the method as described above, wherein the bacterium is *Escherichia coli*.

It is a further aspect of the present invention to provide the method as described above, wherein the bacterium belongs to the genus *Pantoea*.

It is a further aspect of the present invention to provide the method as described above, wherein the bacterium is *Pantoea ananatis*.

It is a further aspect of the present invention to provide the method as described above, wherein the expression of the gshA gene is attenuated due to inactivation of the gshA gene.

It is a further aspect of the present invention to provide the method as described above, wherein the gshA gene is deleted.

It is a further aspect of the present invention to provide the method as described above, wherein the gshA gene is selected from the group consisting of:

(A) a DNA comprising the nucleotide sequence of SEQ ID NO: 1;

(B) a DNA comprising a variant nucleotide sequence of SEQ ID NO: 1 due to the degeneracy of the genetic code;

(C) a DNA having an identity of not less than 60% with respect to the entire nucleotide sequence of SEQ ID NO: 1, and wherein said DNA encodes a protein having an activity of γ-glutamate-cysteine ligase;

(D) a DNA encoding a protein comprising the amino acid sequence of SEQ ID NO: 2; and (E) a DNA encoding a protein comprising the amino acid sequence of SEQ ID NO: 2, but which includes one or more mutations comprising substitution, deletion, insertion, or addition of one or several amino acid residues, and wherein said protein has the activity of γ-glutamate-cysteine ligase.

(F) a DNA encoding a protein having an identity of not less than 65% with respect to the entire amino acid sequence of SEQ ID NO: 2, and wherein said protein has the activity of γ-glutamate-cysteine ligase.

It is a further aspect of the present invention to provide the method as described above, wherein the L-amino acid is selected from the group consisting of an aromatic L-amino acid and a non-aromatic L-amino acid.

It is a further aspect of the present invention to provide the method as described above, wherein the aromatic L-amino acid is selected from the group consisting of L-phenylalanine, L-tryptophan, and L-tyrosine.

It is a further aspect of the present invention to provide the method as described above, wherein the non-aromatic L-amino acid is selected from the group consisting of L-alanine, L-arginine, L-asparagine, L-aspartic acid, L-citrulline, L-cysteine, L-glutamic acid, L-glutamine, glycine, L-histidine, L-isoleucine, L-leucine, L-lysine, L-methionine, L-ornithine, L-proline, L-serine, L-threonine, and L-valine.

It is a further aspect of the present invention to provide the method as described above, wherein the L-amino acid is a branched-chain L-amino acid.

It is a further aspect of the present invention to provide the method as described above, wherein the branched-chain L-amino acid is selected from the group consisting of L-isoleucine, L-leucine, and L-valine.

It is a further aspect of the present invention to provide the method as described above, wherein the L-amino acid is L-valine.

DESCRIPTION OF THE PREFERRED EMBODIMENTS

The present invention is described in detail below.
1. Bacterium

Any L-amino acid-producing bacterium belonging to the family Enterobacteriaceae and modified to attenuate expression of the gshA gene can be used. The phrase "an L-amino acid-producing bacterium" can mean a bacterium of the family Enterobacteriaceae that has an ability to produce, excrete or secrete, and/or cause accumulation of an L-amino acid in a culture medium and/or the bacterial cells when the bacterium is cultured in the medium.

The phrase "an L-amino acid-producing bacterium" can also mean a bacterium that is able to produce, excrete or secrete, and/or cause accumulation of an L-amino acid in a culture medium in an amount larger than a wild-type or parental strain, such as E. coli K-12. The phrase "an L-amino acid-producing bacterium" can also mean a bacterium that is able to cause accumulation in a culture medium of an amount, for example, not less than 0.1 g/L, not less than 0.5 g/L, or not less than 1.0 g/L of the target L-amino acid.

Furthermore, the bacterium belonging to the family Enterobacteriaceae and modified to attenuate expression of the gshA gene, which has an ability to produce L-amino acid, can also be used. The bacterium may inherently have the L-amino acid-producing ability or may be modified to have an L-amino acid-producing ability by using a mutation method or DNA recombination techniques. The bacterium can be obtained by attenuating expression of the gshA gene in a bacterium that inherently has the ability to produce an L-amino acid, or in a bacterium that has been already imparted with the ability to produce an L-amino acid. Alternatively, the bacterium can be obtained by imparting the ability to produce an L-amino acid to a bacterium already modified to attenuate expression of the gshA gene. Also, the bacterium can be a bacterium that has acquired the ability to produce an L-amino acid by attenuating expression of the gshA gene.

The phrase "L-amino acid-producing ability" can mean the ability of the bacterium to produce, excrete or secrete, and/or cause accumulation of the L-amino acid in a culture medium and/or the bacterial cells to such a level that the L-amino acid can be collected from the culture medium and/or the bacterial cells, when the bacterium is cultured in the medium.

The bacterium can produce either one kind of amino acid solely, or a mixture of two or more kinds of amino acids. Specifically, the bacterium can produce either one kind of L-amino acid solely, or a mixture of two or more kinds of L-amino acids.

The phrase "amino acid" can mean an organic compound containing at least one amino group ($NH_2$) and at least one carboxyl group (COOH). An L-amino acid is a non-limiting example of an amino acid.

The phrase "L-amino acid" can mean L-alanine, L-arginine, L-asparagine, L-aspartic acid, L-citrulline, L-cysteine, L-glutamic acid, L-glutamine, glycine, L-histidine, L-isoleucine, L-leucine, L-lysine, L-methionine, L-ornithine, L-phenylalanine, L-proline, L-serine, L-threonine, L-tryptophan, L-tyrosine, and L-valine.

The phrase "aromatic L-amino acid" can include, for example, L-phenylalanine, L-tryptophan, and L-tyrosine. Because L-histidine has an aromatic moiety, specifically, an imidazole ring, the phrase "aromatic L-amino acid" can also include, besides the aforementioned aromatic L-amino acids, L-histidine.

The phrase "non-aromatic L-amino acid" can include, for example, L-alanine, L-arginine, L-asparagine, L-aspartic acid, L-citrulline, L-cysteine, L-glutamic acid, L-glutamine, glycine, L-isoleucine, L-leucine, L-lysine, L-methionine, L-ornithine, L-proline, L-serine, L-threonine, and L-valine. Because the biosynthetic pathway of L-histidine is different from the biosynthetic pathways of common aromatic amino acids such as L-phenylalanine, L-tryptophan, and L-tyrosine, the phrase "non-aromatic L-amino acid" can also include, besides the aforementioned non-aromatic L-amino acids, L-histidine.

That is, L-histidine can be included in either one of, or both of "aromatic L-amino acid" and "non-aromatic L-amino acid".

An L-amino acid can belong to one or more L-amino acid families. As an example, the glutamate family includes L-arginine, L-glutamic acid, L-glutamine, and L-proline; the serine family includes L-cysteine, glycine, and L-serine; the aspartate family includes L-asparagine, L-aspartic acid, L-isoleucine, L-lysine, L-methionine, and L-threonine; the pyruvate family includes L-alanine, L-isoleucine, L-leucine, and L-valine; and the aromatic family includes L-phenylalanine, L-tryptophan, and L-tyrosine. As an L-amino acid can be an intermediate in a biosynthetic pathway of another L-amino acid, the aforementioned families of amino acids may also include other L-amino acids, such as, for example, non-proteinogenic L-amino acids. For example, L-citrulline and L-ornithine are amino acids from the L-arginine biosynthetic pathway. Therefore, the glutamate family may include L-citrulline and L-ornithine, as well as L-arginine, L-glutamic acid, L-glutamine, and L-proline.

An L-amino acid can also belong to one or more L-amino acid groups. As an example, L-isoleucine, L-leucine, and L-valine can belong to the group of branched-chain L-amino acids. Moreover, L-homoleucine and L-homoisoleucine may also belong to the group of branched-chain L-amino acids. L-Alanine, L-isoleucine, L-leucine, L-valine, L-homoleucine, and L-homoisoleucine are particular examples of an L-amino acid. L-Alanine, L-isoleucine, L-leucine, and L-valine are specific examples of an L-amino acid. L-isoleucine, L-leucine, and L-valine are more specific examples of an L-amino acid. L-Valine is an even more specific example of an L-amino acid.

The phrase "L-amino acid" can refer not only to an amino acid in a free form, but may also include a salt or a hydrate of the amino acid, or an adduct formed by the amino acid and another organic or inorganic compound. Salts of amino acids include sulfates, chlorides, carbonates, ammonium salts, sodium salts, potassium salts, hydrochlorides, and so forth. The specific examples of salts of amino acids include, but are not limited to, monochlorhydrate salt of L-lysine (L-lysine.HCl) and monochlorhydrate salt of L-arginine (L-arginine.HCl). Hydrates of amino acids include monohydrates, dihydrates, and so forth. An example of a hydrate of an amino acid includes L-cysteine monohydrate (L-Cys.$H_2O$).

The bacteria belonging to the family Enterobacteriaceae can be from the genera *Enterobacter, Erwinia, Escherichia, Klebsiella, Morganella, Pantoea, Photorhabdus, Providencia, Salmonella, Yersinia*, and so forth, and can have the ability to produce an L-amino acid. Specifically, those classified into the family Enterobacteriaceae according to the taxonomy used in the NCBI (National Center for Biotechnology Information) database (ncbi.nlm.nih.gov/Taxonomy/Browser/wwwtax.cgi?id=543) can be used. Examples of bacteria from the family Enterobacteriaceae that can be modified include a bacterium of the genus *Escherichia, Enterobacter*, or *Pantoea*.

*Escherichia* bacteria which can be modified to obtain *Escherichia* bacteria in accordance with the presently disclosed subject matter are not particularly limited, and specifically, those described in the work of Neidhardt et al. can be used (Bachmann, B. J., Derivations and genotypes of some mutant derivatives of *E. coli* K-12, p. 2460-2488. In F. C. Neidhardt et al. (ed.), *E. coli* and *Salmonella*: cellular and molecular biology, $2^{nd}$ ed. ASM Press, Washington, D.C., 1996). The species *E. coli* is a particular example. Specific examples of *E. coli* include *E. coli* W3110 (ATCC 27325), *E. coli* MG1655 (ATCC 47076), and so forth, which are derived from the prototype wild-type strain, *E. coli* K-12 strain. These strains are available from, for example, the American Type Culture Collection (10801 University Boulevard, Manassas, Va. 20110, United States of America). That is, registration numbers are given to each of the strains, and the strains can be ordered by using these registration numbers (refer to atcc.org). The registration numbers of the strains are listed in the catalogue of the American Type Culture Collection.

Examples of the *Enterobacter* bacteria include *Enterobacter agglomerans, Enterobacter aerogenes*, and so forth. Examples of the *Pantoea* bacteria include *Pantoea ananatis* (*P. ananatis*), and so forth. Some strains of *Enterobacter agglomerans* were recently reclassified into *Pantoea agglomerans, Pantoea ananatis*, or *Pantoea stewartii* on the basis of nucleotide sequence analysis of 16S rRNA, etc. A bacterium belonging to either genus *Enterobacter* or *Pantoea* may be used so long as it is a bacterium classified into the family Enterobacteriaceae. When a *P. ananatis* strain is bred by genetic engineering techniques, *P. ananatis* AJ13355 strain (FERM BP-6614), AJ13356 strain (FERM BP-6615), AJ13601 strain (FERM BP-7207), and derivatives thereof can be used. These strains were identified as *Enterobacter agglomerans* when they were isolated, and deposited as *Enterobacter agglomerans*. However, they were recently re-classified as *Pantoea ananatis* on the basis of nucleotide sequencing of 16S rRNA and so forth as described above.

Hereafter, L-amino acid-producing bacteria will be specifically exemplified. Any of the properties of the L-amino acid-producing bacteria and modifications for imparting or enhancing an L-amino acid-producing ability, such as those exemplified below, can be used independently or in any appropriate combination.

L-Arginine-Producing Bacteria

Examples of L-arginine-producing bacteria and parental strains which can be used to derive L-arginine-producing bacteria include, but are not limited to, strains belonging to the genus *Escherichia* such as *E. coli* strain 237 (VKPM B-7925) (U.S. Patent Application No. 2002058315 A1) and its derivative strains harboring mutant N-acetylglutamate synthase (Russian Patent No. 2215783 C2), *E. coli* strain 382 (VKPM B-7926, EP1170358 A1), which is a strain derived from the strain 237 and having an improved acetic acid-assimilating ability, *E. coli* strain 382 ilvA+, which is a strain obtained from the strain 382 by introducing the wild-type allele of ilvA gene from *E. coli* K-12 strain thereto, and the like. Examples of mutant N-acetylglutamate synthase include, for example, a mutant N-acetylglutamate synthase desensitized to feedback inhibition by L-arginine by substitution for the amino acid residues corresponding to the positions 15 to 19 of the wild type enzyme (EP1170361 A1).

Examples of L-arginine-producing bacteria and parental strains which can be used to derive L-arginine-producing bacteria also include strains in which expression of one or more genes encoding an L-arginine biosynthetic enzyme are enhanced. Examples of such genes include genes encoding N-acetyl-γ-glutamylphosphate reductase (argC), ornithine acetyltransferase (argJ), N-acetylglutamate kinase (argB), N-acetylornithine aminotransferase (argD), ornithine carbamoyltransferase (argI, argininosuccinate synthase (argG), argininosuccinate lyase (argH), and carbamoyl phosphate synthetase (carAB), in addition to the gene encoding N-acetylglutamate synthase (argA).

Examples of L-arginine-producing bacteria and parental strains which can be used to derive L-arginine-producing bacteria also can include strains having resistance to amino acid analogues, and so forth. Examples of such strains include *Escherichia coli* mutant strains having resistance to α-methylmethionine, p-fluorophenylalanine, D-arginine, arginine hydroxamate, S-(2-aminoethyl)-cysteine, α-methylserine, β-2-thienylalanine, or sulfaguanidine (refer to Japanese Patent Laid-open (Kokai) No. 56-106598).

L-Citrulline-Producing Bacteria

Examples of L-citrulline-producing bacteria and parental strains which can be used to derive L-citrulline-producing bacteria include, but are not limited to, strains belonging to the genus *Escherichia* such as *E. coli* strains 237/pMADS11, 237/pMADS12, and 237/pMADS13 (RU2215783 C2, European Patent No. 1170361 B1, U.S. Pat. No. 6,790,647 B2), which harbor mutant N-acetylglutamate synthase, *E. coli* strains 333 (VKPM B-8084) and 374 (VKPM B-8086), both harboring mutant feedback-resistant carbamoyl phosphate synthetase (Russian Patent No. 2264459 C2), *E. coli* strains in which α-ketoglutarate synthase activity is increased, and ferredoxin NADP$^+$ reductase, pyruvate synthase, and/or α-ketoglutarate dehydrogenase activities are additionally modified (EP2133417 A1), and *P. ananantis* strain NA1sucAsdhA, in which succinate dehydrogenase and α-ketoglutarate dehydrogenase activities are decreased (U.S. Patent Application No. 2009286290 A1), and the like.

As L-citrulline is an intermediate of L-arginine biosynthetic pathway, examples of L-citrulline-producing bacteria and parent strains which can be used to derive L-citrulline-producing bacteria, include strains in which expression of one or more genes encoding an L-arginine biosynthetic enzyme is enhanced. Examples of such genes include, but are not limited to, genes encoding N-acetylglutamate synthase (argA), N-acetylglutamate kinase (argB), N-acetylglutamyl phosphate reductase (argC), acetylornithine transaminase (argD), acetylornithine deacetylase (argE), ornithine carbamoyltransferase (argF/1), and carbamoyl phosphate synthetase (carAB), and combinations thereof.

An L-citrulline-producing bacterium can be also easily obtained from any L-arginine-producing bacterium, for example *E. coli* 382 strain (VKPM B-7926), by inactivation of argininosuccinate synthase encoded by argG gene.

L-Cysteine-Producing Bacteria

Examples of L-cysteine-producing bacteria and parental strains which can be used to derive L-cysteine-producing bacteria include, but are not limited to, strains belonging to the genus *Escherichia* such as *E. coli* JM15 transformed with different cysE alleles encoding feedback-resistant serine acetyltransferases (U.S. Pat. No. 6,218,168 B1, Russian Patent No. 2279477 C2), *E. coli* W3110 having overexpressed genes which encode proteins suitable for secreting substances toxic for cells (U.S. Pat. No. 5,972,663 A), *E. coli* strains having a lowered cysteine desulfhydrase activity (JP11155571 A2), *E. coli* W3110 having an increased activity of a positive transcriptional regulator for cysteine regulation encoded by the cysB gene (WO0127307 A1), and the like. Examples of L-cysteine-producing bacteria and parental strains which can be used to derive L-cysteine-producing bacteria also include *E. coli* strain JM15(ydeD), which is a derivative of *E. coli* JM15 (U.S. Pat. No. 6,218,168 B1, and has been transformed with DNA containing the ydeD gene (U.S. Pat. No. 5,972,663).

L-Glutamic Acid-Producing Bacteria

Examples of L-glutamic acid-producing bacteria and parental strains which can be used to derive L-glutamic acid-producing bacteria include, but are not limited to, strains belonging to the genus *Escherichia* such as *E. coli* VL334thrC$^+$ (EP 1172433 A1). The *E. coli* VL334 (VKPM B-1641) is an L-isoleucine and L-threonine auxotrophic strain having mutations in thrC and ilvA genes (U.S. Pat. No. 4,278,765). A wild-type allele of the thrC gene was transferred by the method of general transduction using a bacteriophage P1 grown on the wild-type *E. coli* strain K-12 (VKPM B-7) cells. As a result, an L-isoleucine auxotrophic strain VL334thrC$^+$ (VKPM B-8961), which is able to produce L-glutamic acid, was obtained.

Examples of L-glutamic acid-producing bacteria and parental strains which can be used to derive the L-glutamic acid-producing bacteria include, but are not limited to, strains in which expression of one or more genes encoding an L-glutamic acid biosynthetic enzyme are enhanced. Examples of such genes include genes encoding glutamate dehydrogenase (gdhA), glutamine synthetase (glnA), glutamate synthetase (gltBD), isocitrate dehydrogenase (icdA), aconitate hydratase (acnA, acnB), citrate synthase (gltA), pyruvate carboxylase (pyc), pyruvate dehydrogenase (aceEF, lpdA), pyruvate kinase (pykA, pykF), phosphoenolpyruvate synthase (ppsA), enolase (eno), phosphoglyceromutase (pgmA, pgm1), phosphoglycerate kinase (pgk), glyceraldehyde-3-phophate dehydrogenase (gapA), triose phosphate isomerase (tpiA), fructose bisphosphate aldolase (fbp), and glucose phosphate isomerase (pgi).

Examples of strains modified so that expression of the citrate synthetase gene, the phosphoenolpyruvate carboxylase gene, and/or the glutamate dehydrogenase gene is/are enhanced include those disclosed in EP1078989 A2, EP955368 A2, and EP952221 A2.

Examples of L-glutamic acid-producing bacteria and parental strains which can be used to derive the L-glutamic acid-producing bacteria also include strains having a decreased or eliminated activity of an enzyme that catalyzes synthesis of a compound other than L-glutamic acid by branching off from an L-glutamic acid biosynthesis pathway. Examples of such enzymes include isocitrate lyase (aceA), α-ketoglutarate dehydrogenase (sucA), acetolactate synthase (ilvl), formate acetyltransferase (pfl), lactate dehydrogenase (ldh), glutamate decarboxylase (gadAB), and succinate dehydrogenase (sdhABCD). Shown in the parentheses after the names of the enzymes are examples of the genes encoding the enzymes (the same shall apply similarly throughout this specification). Bacteria belonging to the genus *Escherichia* deficient in α-ketoglutarate dehydrogenase activity or having reduced α-ketoglutarate dehydrogenase activity and methods for obtaining them are described in U.S. Pat. Nos. 5,378,616 and 5,573,945. Specifically, these strains include the following:

*E. coli* W3110sucA::Km$^R$,
*E. coli* AJ12624 (FERM BP-3853),
*E. coli* AJ12628 (FERM BP-3854),
*E. coli* AJ12949 (FERM BP-4881).

*E. coli* W3110sucA::Km$^R$ is a strain obtained by disrupting the α-ketoglutarate dehydrogenase gene (hereinafter referred to as "sucA gene") of *E. coli* W3110. This strain is completely deficient in α-ketoglutarate dehydrogenase.

Other examples of L-glutamic acid-producing bacteria and parental strains which can be used to derive the L-glutamic acid-producing bacteria include strains that belong to the genus *Escherichia* and have resistance to an aspartic acid antimetabolite (aspartic acid analogue). These strains can also be deficient in α-ketoglutarate dehydrogenase activity and examples thereof include, for example, *E. coli* AJ13199 (FERM BP-5807) (U.S. Pat. No. 5,908,768), *E. coli* FFRM P-12379, which additionally has a lowered L-glutamic acid-decomposing ability (U.S. Pat. No. 5,393,671), *E. coli* AJ13138 (FERM BP-5565) (U.S. Pat. No. 6,110,714), and the like.

Examples of L-glutamic acid-producing bacteria and parental strains which can be used to derive the L-glutamic acid-producing bacteria also include *Pantoea* bacteria, such as the *P. ananatis* AJ13355 strain (FERM BP-6614), *P. ananatis* SC17 strain (FERM BP-11091), and *P. ananatis* SC17(0) strain (VKPM B-9246). The AJ13355 strain is a strain isolated from soil in Iwata-shi, Shizuoka-ken, Japan as a strain that can proliferate in a low pH medium containing L-glutamic acid and a carbon source. The SC17 strain is a strain selected as a low phlegm-producing mutant strain from the AJ13355 strain (U.S. Pat. No. 6,596,517). The SC17 strain was deposited at the independent administrative agency, National Institute of Advanced Industrial Science and Technology, International Patent Organism Depositary (currently, independent administrative agency, National Institute of Technology and Evaluation, International Patent Organism Depositary (NITE IPOD), #120, 2-5-8 Kazusakamatari, Kisarazu-shi, Chiba-ken, 292-0818, Japan) on Feb. 4, 2009, and assigned an accession number of FERM BP-11091. The AJ13355 strain was deposited at the National Institute of Bioscience and Human Technology, Agency of Industrial Science and Technology, Ministry of International Trade and Industry (currently, NITE IPOD, #120, 2-5-8 Kazusakamatari, Kisarazu-shi, Chiba-ken, 292-0818, Japan) on Feb. 19, 1998 and assigned an accession number of FERM P-16644. Then, the deposit was converted to an international deposit under the provisions of the Budapest Treaty on Jan. 11, 1999, and assigned an accession number of FERM BP-6614.

Examples of L-glutamic acid-producing bacteria and parental strains which can be used to derive the L-glutamic acid-producing bacteria also include mutant strains belonging to the genus *Pantoea* that are deficient in α-ketoglutarate dehydrogenase activity or have decreased α-ketoglutarate dehydrogenase activity, and can be obtained as described above. Such strains include *P. ananatis* AJ13356 (U.S. Pat. No. 6,331,419 B1). *P. ananatis* AJ13356 was deposited at the National Institute of Bioscience and Human-Technology, Agency of Industrial Science and Technology, Ministry of International Trade and Industry (currently, NITE IPOD, #120, 2-5-8 Kazusakamatari, Kisarazu-shi, Chiba-ken, 292-0818, Japan) on Feb. 19, 1998 under the accession number FERM P-16645. It was then converted to an international deposit under the provisions of the Budapest Treaty on Jan. 11, 1999 and received an accession number of FERM BP-6615. *P. ananatis* AJ13356 is deficient in α-ketoglutarate dehydrogenase activity as a result of disruption of the αKGDH-E1 subunit gene (sucA). The above strain was identified as *Enterobacter agglomerans* when it was isolated and deposited as the *Enterobacter agglomerans* AJ13356. However, it was recently re-classified as *Pantoea ananatis* on the basis of nucleotide sequencing of 16S rRNA and so forth. Although AJ13356 was deposited at the aforementioned depository as *Enterobacter agglomerans*, for the purposes of this specification, they are described as *P. ananatis*.

Examples of L-glutamic acid-producing bacteria and parental strains which can be used to derive the L-glutamic acid-producing bacteria also include strains belonging to the genus *Pantoea* such as the *P. ananatis* SC17sucA/RSFCPG+pSTVCB strain, *P. ananatis* AJ13601 strain, *P. ananatis* NP106 strain, and *P. ananatis* NA1 strain. The SC17sucA/RSFCPG+pSTVCB strain was obtained by introducing the plasmid RSFCPG containing the citrate synthase gene (gltA), phosphoenolpyruvate carboxylase gene (ppc), and glutamate dehydrogenase gene (gdhA) derived from *Escherichia coli*, and the plasmid pSTVCB containing the citrate synthase gene (gltA) derived from *Brevibacterium lactofermentum*, into the SC17sucA strain. The AJ13601 strain is a strain selected from the SC17sucA/RSFCPG+pSTVCB strain as a strain resistant to a high concentration of L-glutamic acid at a low pH. The NP106 strain was obtained from the AJ13601 strain by curing the RSFCPG and pSTVCB plasmids. The AJ13601 strain was deposited at the National Institute of Bioscience and Human Technology, Agency of Industrial Science and Technology, Ministry of International Trade and Industry (currently, NITE IPOD, #120, 2-5-8 Kazusakamatari, Kisarazu-shi, Chiba-ken, 292-0818, Japan) on Aug. 18, 1999, and assigned an accession number FERM P-17516. Then, the deposit was converted to an international deposit under the provisions of the Budapest Treaty on Jul. 6, 2000, and assigned an accession number FERM BP-7207.

L-Histidine-Producing Bacteria

Examples of L-histidine-producing bacteria and parental strains which can be used to derive L-histidine-producing bacteria include, but are not limited to, strains belonging to the genus *Escherichia* such as *E. coli* strain 24 (VKPM B-5945, RU2003677 C1), *E. coli* strain 80 (VKPM B-7270, RU2119536 C1), *E. coli* NRRL B-12116-B-12121 (U.S. Pat. No. 4,388,405), *E. coli* H-9342 (FERM BP-6675) and H-9343 (FERM BP-6676) (U.S. Pat. No. 6,344,347 B1), *E. coli* H-9341 (FERM BP-6674) (EP1085087 A2), *E. coli* AI80/pFM201 (U.S. Pat. No. 6,258,554 B1), and the like.

Examples of L-histidine-producing bacteria and parental strains which can be used to derive L-histidine-producing bacteria also include strains in which expression of one or more genes encoding an L-histidine biosynthetic enzyme are enhanced. Examples of such genes include genes encoding ATP phosphoribosyltransferase (hisG), phosphoribosyl-AMP cyclohydrolase (his1), phosphoribosyl-AMP cyclohydrolase/phosphoribosyl-ATP pyrophosphatase (hisIE), phosphoribosylformimino-5-aminoimidazole carboxamide ribotide isomerase (hisA), amidotransferase (hisH), histidinol phosphate aminotransferase (hisC), histidinol phosphatase (hisB), histidinol dehydrogenase (hisD), and so forth.

It is known that the L-histidine biosynthetic enzymes encoded by hisG and hisBHAFI are inhibited by L-histidine, and therefore an L-histidine-producing ability can also be efficiently enhanced by introducing a mutation conferring resistance to the feedback inhibition into ATP phosphoribosyltransferase (Russian Patent Nos. 2003677 C1 and 2119536 C1).

Specific examples of strains having an L-histidine-producing ability include *E. coli* FERM-P 5038 and 5048, which have been transformed with a vector carrying a DNA encoding an L-histidine-biosynthetic enzyme (JP 56-005099 A), *E. coli* strains transformed with rht, a gene for an amino acid-export (EP1016710 A2), *E. coli* 80 strain, which has been imparted with sulfaguanidine, DL-1,2,4-triazole-3-alanine, and streptomycin-resistance (VKPM B-7270, RU2119536 C1), *E. coli* MG1655+hisGr hisL'_Δ ΔpurR (RU2119536 and Doroshenko V. G. et al., The directed modification of *Escherichia coli* MG1655 to obtain histidine-producing mutants, *Prikl. Biochim. Mikrobiol.* (*Russian*), 2013, 49(2):149-154), and so forth.

L-Isoleucine-Producing Bacteria

Examples of L-isoleucine-producing bacteria and parental strains which can be used to derive L-isoleucine-producing bacteria include, but are not limited to, mutant strains having resistance to 6-dimethylaminopurine (JP 5-304969 A), mutant strains having resistance to an isoleucine analogue such as thiaisoleucine and isoleucine hydroxamate, and mutant strains additionally having resistance to DL-ethionine and/or arginine hydroxamate (JP 5-130882 A). In addition, recombinant strains transformed with genes encoding proteins involved in L-isoleucine biosynthesis, such as threonine deaminase and acetohydroxate synthase, can also be used as L-isoleucine-producing bacteria or parental strains thereof (JP 2-458 A, EP0356739 A1, and U.S. Pat. No. 5,998,178).

L-Leucine-Producing Bacteria

Examples of L-leucine-producing bacteria and parental strains which can be used to derive L-leucine-producing bacteria include, but are not limited to, strains belonging to the genus *Escherichia* such as *E. coli* strains resistant to leucine (for example, the strain 57 (VKPM B-7386, U.S. Pat. No. 6,124,121)); *E. coli* strains resistant to leucine analogs including R-2-thienylalanine, 3-hydroxyleucine, 4-azaleucine, 5,5,5-trifluoroleucine (JP 62-34397 B and JP 8-70879 A); *E. coli* strains obtained by the gene engineering method described in WO96/06926; *E. coli* H-9068 (JP 8-70879 A), and the like.

Examples of L-leucine-producing bacteria and parental strains which can be used to derive L-leucine-producing bacteria also include strains in which the expression of one or more genes involved in L-leucine biosynthesis is enhanced. Examples of such genes include genes of the leuABCD operon, which can be represented by a mutant leuA gene encoding α-isopropylmalate synthase freed from feedback inhibition by L-leucine (U.S. Pat. No. 6,403,342 B1). In addition, examples of L-leucine-producing bacteria and parental strains which can be used to derive L-leucine-producing bacteria also include strains in which the expression of one or more genes encoding proteins which excrete L-amino acid from the bacterial cell is enhanced. Examples of such genes include the b2682 and b2683 genes (ygaZH genes) (EP1239041 A2).

L-Lysine-Producing Bacteria

Examples of L-lysine-producing bacteria and parental strains which can be used to derive L-lysine-producing bacteria include mutant strains belonging to the genus *Escherichia* and having resistance to an L-lysine analogue. The L-lysine analogue inhibits growth of bacteria belonging to the genus *Escherichia*, but this inhibition is fully or partially desensitized when L-lysine is present in the medium. Examples of the L-lysine analogue include, but are not limited to, oxalysine, lysine hydroxamate, S-(2-aminoethyl)-L-cysteine (AEC), γ-methyllysine, α-chlorocaprolactam, and so forth. Mutant strains having resistance to these lysine analogues can be obtained by subjecting bacteria belonging to the genus *Escherichia* to a conventional artificial mutagenesis treatment. Specific examples of bacterial strains useful for producing L-lysine include *E. coli* AJ11442 (FERM BP-1543, NRRL B-12185; see U.S. Pat. No. 4,346,170) and *E. coli* VL611. In these strains, feedback inhibition of aspartokinase by L-lysine is desensitized.

Examples of L-lysine-producing bacteria and parental strains which can be used to derive L-lysine-producing bacteria also include strains in which expression of one or more genes encoding an L-lysine biosynthetic enzyme is enhanced. Examples of such genes include, but are not limited to, genes encoding dihydrodipicolinate synthase (dapA), aspartokinase III (lysC), dihydrodipicolinate reductase (dapB), diaminopimelate decarboxylase (lysA), diaminopimelate dehydrogenase (ddh) (U.S. Pat. No. 6,040, 160), phosphoenolpyruvate carboxylase (ppc), aspartate semialdehyde dehydrogenase (asd), and aspartase (aspA) (EP1253195 A1). In addition, the L-lysine-producing bacteria or parental strains thereof may have an increased level of expression of the gene involved in energy efficiency (cyo) (EP1170376 A1), the gene encoding nicotinamide nucleotide transhydrogenase (pntAB) (U.S. Pat. No. 5,830,716 A), the ybjE gene (WO2005/073390), or combinations thereof. Since aspartokinase III is subject to feedback inhibition by L-lysine, a mutant lysC gene coding for an aspartokinase III desensitized to feedback inhibition by L-lysine (U.S. Pat. No. 5,932,453) may be used for enhancing the activity of this enzyme. Further, since dihydrodipicolinate synthase is subject to feedback inhibition by L-lysine, a mutant dapA gene coding for a dihydrodipicolinate synthase desensitized to feedback inhibition by L-lysine may be used for enhancing the activity of this enzyme.

L-Lysine-producing bacteria or parental strains which can be used to derive L-lysine-producing bacteria may have a reduced or no activity of an enzyme that catalyzes a reaction which causes a branching off from the L-lysine biosynthesis pathway and results in the production of another compound. Also, L-lysine-producing bacteria or parental strains which can be used to derive L-lysine-producing bacteria may have a reduced or no activity of an enzyme that negatively acts on L-lysine synthesis or accumulation. Examples of such enzymes involved in L-lysine production include homoserine dehydrogenase, lysine decarboxylase (cadA, ldcC), malic enzyme, and so forth, and strains in which activities of these enzymes are decreased or deleted are disclosed in WO95/23864, WO96/17930, WO2005/010175, and so forth.

Expression of both the cadA and ldcC genes encoding lysine decarboxylase can be decreased in order to decrease or delete the lysine decarboxylase activity. Expression of the both genes can be decreased by, for example, the method described in WO2006/078039.

Examples of L-lysine-producing bacteria and parental strains which can be used to derive L-lysine-producing bacteria also include the *E. coli* WC196 strain (U.S. Pat. No. 5,827,698), the *E. coli* WC196ΔcadAΔldc strain, and the *E. coli* WC196ΔcadAΔldcC/pCABD2 strain (WO2006/078039).

The WC196 strain was bred from the W3110 strain, which was derived from *E. coli* K-12, by conferring AEC resistance to the W3110 strain (U.S. Pat. No. 5,827,698). The WC196 strain was designated *E. coli* AJ13069, deposited at the National Institute of Bioscience and Human-Technology, Agency of Industrial Science and Technology (currently, NITE IPOD, #120, 2-5-8 Kazusakamatari, Kisarazu-shi, Chiba-ken, 292-0818, Japan) on Dec. 6, 1994, and assigned an accession number of FERM P-14690. Then, it was converted to an international deposit under the provisions of the Budapest Treaty on Sep. 29, 1995, and assigned an accession number of FERM BP-5252 (U.S. Pat. No. 5,827, 698).

The WC196ΔcadAΔldc strain was constructed from the WC196 strain by disrupting the cadA and ldcC genes which encode lysine decarboxylase. The WC196ΔcadAΔldcC was designated AJ110692 and deposited at the independent administrative agency, National Institute of Advanced Industrial Science and Technology, International Patent Organism Depositary (currently, NITE IPOD, #120, 2-5-8 Kazusakamatari, Kisarazu-shi, Chiba-ken, 292-0818, Japan) on Oct. 7, 2008 as an international deposit under the accession number FERM BP-11027.

The WC196ΔcadAΔldcC/pCABD2 strain was constructed by introducing the plasmid pCABD2 containing lysine biosynthesis genes (U.S. Pat. No. 6,040,160) into the WC196ΔcadAΔldcC strain. The plasmid pCABD2 contains a mutant dapA gene derived from *Escherichia coli* and coding for a dihydrodipicolinate synthase (DDPS) having a mutation for desensitization to feedback inhibition by L-lysine (H118Y), a mutant lysC gene derived from *Escherichia coli* and coding for aspartokinase III having a mutation for desensitization to feedback inhibition by L-lysine (T352I), the dapB gene derived from *Escherichia coli* and coding for dihydrodipicolinate reductase, and the ddh gene derived from *Brevibacterium lactofermentum* and coding for diaminopimelate dehydrogenase.

Examples of L-lysine-producing bacteria and parental strains which can be used to derive L-lysine-producing bacteria also include *E. coli* AJIK01 (NITE BP-01520). The AJIK01 strain was designated *E. coli* AJ111046, and deposited at NITE IPOD (#120, 2-5-8 Kazusakamatari, Kisarazu-shi, Chiba-ken, 292-0818, Japan) on Jan. 29, 2013. Then, it was converted to an international deposit under the provisions of the Budapest Treaty on May 15, 2014, and assigned an accession number of NITE BP-01520.

L-Methionine-Producing Bacteria

Examples of L-methionine-producing bacteria and parent strains which can be used to derive L-methionine-producing bacteria include, but are not limited to, strains belonging to the genus *Escherichia* such as *E. coli* strains AJ11539 (NRRL B-12399), AJ11540 (NRRL B-12400), AJ11541 (NRRL B-12401), AJ 11542 (NRRL B-12402) (Patent GB2075055); and *E. coli* strains 218 (VKPM B-8125) (RU2209248 C2) and 73 (VKPM B-8126) (RU2215782 C2) resistant to norleucine, the L-methionine analog, or the like. The strain *E. coli* was deposited in the Russian National Collection of Industrial Microorganisms (VKPM; Russian Federation, 117545 Moscow, $1^{st}$ Dorozhny proezd, 1) on May 14, 2001 under the accession number VKPM B-8126. Then, it was converted to an international deposit under the provisions of the Budapest Treaty on Feb. 1, 2002. Furthermore, a methionine repressor-deficient strain and recombinant strains transformed with genes encoding proteins involved in L-methionine biosynthesis such as homoserine transsuccinylase and cystathionine γ-synthase (JP 2000-139471 A) can also be used as L-methionine-producing bacteria or parent strains thereof.

L-Ornithine-Producing Bacteria

As L-ornithine is an intermediate of L-arginine biosynthetic pathway, examples of L-ornithine-producing bacteria and parent strains which can be used to derive L-ornithine-producing bacteria, include strains in which expression of one or more genes encoding an L-arginine biosynthetic enzyme, such as those described above, is enhanced.

An L-ornithine-producing bacterium can be easily obtained from any L-arginine-producing bacterium, for example *E. coli* 382 strain (VKPM B-7926), by inactivation of ornithine carbamoyltransferase encoded by both argF and argI genes. Methods for inactivation of ornithine carbamoyltransferase are described herein.

L-Phenylalanine-Producing Bacteria

Examples of L-phenylalanine-producing bacteria and parental strains which can be used to derive L-phenylalanine-producing bacteria include, but are not limited to, strains belonging to the genus *Escherichia* such as *E. coli* AJ12739 (tyrA::Tn10, tyrR) (VKPM B-8197), *E. coli* HW1089 (ATCC 55371) harboring the mutant pheA34 gene (U.S. Pat. No. 5,354,672), *E. coli* MWEC101-b (KR8903681), *E. coli* NRRL B-12141, NRRL B-12145, NRRL B-12146, and NRRL B-12147 (U.S. Pat. No. 4,407,952), *E. coli* K-12 [W3110 (tyrA)/pPHAB] (FERM BP-3566), *E. coli* K-12 [W3110 (tyrA)/pPHAD] (FERM BP-12659), *E. coli* K-12 [W3110 (tyrA)/pPHATerm] (FERM BP-12662), and *E. coli* K-12 [W3110 (tyrA)/pBR-aroG4, pACMAB] named as AJ12604 (FERM BP-3579) (EP488424 B1). Furthermore, L-phenylalanine-producing bacteria and parental strains which can be used to derive L-phenylalanine-producing bacteria also include strains belonging to the genus *Escherichia* and having an enhanced activity of the protein encoded by the yedA gene or the yddG gene (U.S. Pat. Nos. 7,259,003 and 7,666,655).

L-Proline-Producing Bacteria

Examples of L-proline-producing bacteria and parental strains which can be used to derive L-proline-producing bacteria include, but are not limited to, strains belonging to the genus *Escherichia* such as *E. coli* 702ilvA (VKPM B-8012), which is deficient in the ilvA gene and is able to produce L-proline (EP1172433 A1). Examples of L-proline-producing bacteria and parental strains which can be used to derive L-proline-producing bacteria also include strains in which the expression of one or more genes involved in L-proline biosynthesis is enhanced. Examples of such genes which can be used in L-proline-producing bacteria include the proB gene encoding glutamate kinase with desensitized feedback inhibition by L-proline (DE3127361 A1). In addition, examples of L-proline-producing bacteria and parental strains which can be used to derive L-proline-producing bacteria also include strains in which the expression of one or more genes encoding proteins responsible for excreting L-amino acid from the bacterial cell is enhanced. Examples of such genes include the b2682 and b2683 genes (ygaZH genes) (EP1239041 A2).

Examples of bacteria belonging to the genus *Escherichia* that have an ability to produce L-proline include the following *E. coli* strains: NRRL B-12403 and NRRL B-12404 (GB Patent 2075056), VKPM B-8012 (Russian Patent No. 2207371 C2), plasmid mutants described in DE3127361 A1, plasmid mutants described by Bloom F. R. et al. in "The $15^{th}$ Miami winter symposium", 1983, p. 34, and the like.

L-Threonine-Producing Bacteria

Examples of L-threonine-producing bacteria and parental strains which can be used to derive L-threonine-producing bacteria include, but are not limited to, strains belonging to the genus *Escherichia* such as *E. coli* TDH-6/pVIC40 (VKPM B-3996) (U.S. Pat. Nos. 5,175,107 and 5,705,371), *E. coli* 472T23/pYN7 (ATCC 98081) (U.S. Pat. No. 5,631,157), *E. coli* NRRL B-21593 (U.S. Pat. No. 5,939,307), *E. coli* FERM BP-3756 (U.S. Pat. No. 5,474,918), *E. coli* FERM BP-3519 and FERM BP-3520 (U.S. Pat. No. 5,376,538), *E. coli* MG442 (Gusyatiner M. et al., *Genetika* (*Russian*), 1978, 14:947-956), *E. coli* VL643 and VL2055 (EP1149911 A2), *E. coli* VKPM B-5318 (EP0593792 A1), and the like.

The strain TDH-6 is deficient in the thrC gene, as well as being sucrose-assimilative, and the ilvA gene thereof has a leaky mutation. This strain also has a mutation in the rhtA gene, which mutation imparts resistance to high concentrations of threonine or homoserine. The strain VKPM B-3996, which contains the plasmid pVIC40, was obtained by introducing the plasmid pVIC40 into the TDH-6 strain. The plasmid pVIC40 was obtained by inserting a thrA*BC operon which includes a mutant thrA gene into a RSF1010-derived vector. This mutant thrA gene encodes aspartokinase homoserine dehydrogenase I which has substantially desensitized feedback inhibition by threonine. The strain VKPM B-3996 was deposited on Nov. 19, 1987 in the All-Union Scientific Center of Antibiotics (Russian Federation, 117105 Moscow, Nagatinskaya Street 3-A) under the accession number RIA 1867. The strain VKPM B-3996 was also deposited in the Russian National Collection of Industrial Microorganisms (VKPM; FGUP GosNII Genetika, Russian Federation, 117545 Moscow, $1^{st}$ Dorozhny proezd, 1) on Apr. 7, 1987 under the accession number VKPM B-3996.

The strain B-5318 is prototrophic with regard to isoleucine; and harbors the plasmid pPRT614, which corresponds to the plasmid pVIC40 of which the regulatory region of the threonine operon is replaced with a temperature-sensitive lambda-phage C1 repressor and PR promoter. The strain VKPM B-5318 was deposited in the Russian National Collection of Industrial Microorganisms (VKPM) on May 3, 1990 under the accession number VKPM B-5318.

L-Threonine-producing bacteria or parental strains which can be used to derive L-threonine-producing bacteria can be modified to enhance expression of one or more of the following genes:

the mutant thrA gene which encodes aspartokinase homoserine dehydrogenase I resistant to feedback inhibition by threonine;
the thrB gene which encodes homoserine kinase;
the thrC gene which encodes threonine synthase;
the rhtA gene which encodes a putative transmembrane protein of the threonine and homoserine efflux system;
the asd gene which encodes aspartate-β-semialdehyde dehydrogenase; and
the aspC gene which encodes aspartate aminotransferase (aspartate transaminase);

The thrA gene which encodes aspartokinase I and homoserine dehydrogenase I of *E. coli* has been elucidated (KEGG, Kyoto Encyclopedia of Genes and Genomes, entry No. b0002; GenBank, accession No. NC_000913.2; nucleotide positions: 337 to 2,799; Gene ID: 945803). The thrA gene is located between the thrL and thrB genes on the chromosome of *E. coli* K-12.

The thrB gene which encodes homoserine kinase of *E. coli* has been elucidated (KEGG, entry No. b0003; GenBank, accession No. NC_000913.2; nucleotide positions: 2,801 to 3,733; Gene ID: 947498). The thrB gene is located between the thrA and thrC genes on the chromosome of *E. coli* K-12.

The thrC gene which encodes threonine synthase of *E. coli* has been elucidated (KEGG, entry No. b0004; GenBank, accession No. NC_000913.2; nucleotide positions: 3,734 to 5,020; Gene ID: 945198). The thrC gene is located between the thrB and yaaX genes on the chromosome of *E. coli* K-12. All three genes function as a single threonine operon thrABC. To enhance expression of the threonine operon, the attenuator region which affects the transcription is desirably removed from the operon (WO2005049808 A1, WO2003097839 A1).

The mutant thrA gene which encodes aspartokinase I and homoserine dehydrogenase I resistant to feedback inhibition by L-threonine, as well as, the thrB and thrC genes can be obtained as one operon from the well-known plasmid pVIC40 which is present in the L-threonine-producing *E. coli* strain VKPM B-3996. Plasmid pVIC40 is described in detail in U.S. Pat. No. 5,705,371.

The rhtA gene which encodes a protein of the threonine and homoserine efflux system (an inner membrane transporter) of *E. coli* has been elucidated (KEGG, entry No. b0813; GenBank, accession No. NC_000913.2; nucleotide positions: 848,433 to 849,320, complement; Gene ID: 947045). The rhtA gene is located between the dps and ompX genes on the chromosome of *E. coli* K-12 close to the glnHPQ operon, which encodes components of the glutamine transport system. The rhtA gene is identical to the ybiF gene (KEGG, entry No. b0813).

The asd gene which encodes aspartate-β-semialdehyde dehydrogenase of *E. coli* has been elucidated (KEGG, entry No. b3433; GenBank, accession No. NC_000913.2; nucleotide positions: 3,571,798 to 3,572,901, complement; Gene ID: 947939). The asd gene is located between the glgB and gntU gene on the same strand (yhgN gene on the opposite strand) on the chromosome of *E. coli* K-12.

Also, the aspC gene which encodes aspartate aminotransferase of *E. coli* has been elucidated (KEGG, entry No. b0928; GenBank, accession No. NC_000913.2; nucleotide positions: 983,742 to 984,932, complement; Gene ID: 945553). The aspC gene is located between the ycbL gene on the opposite strand and the ompF gene on the same strand on the chromosome of *E. coli* K-12.

L-Tryptophan-Producing Bacteria

Examples of L-tryptophan-producing bacteria and parental strains which can be used to derive the L-tryptophan-producing bacteria include, but are not limited to, strains belonging to the genus *Escherichia* such as *E. coli* JP4735/pMU3028 (DSM10122) and JP6015/pMU91 (DSM10123), which have a mutant trpS gene encoding a partially inactivated tryptophanyl-tRNA synthetase (U.S. Pat. No. 5,756,345), *E. coli* SV164 (pGH5) having a serA allele encoding phosphoglycerate dehydrogenase free from feedback inhibition by serine and a trpE allele encoding anthranilate synthase free from feedback inhibition by tryptophan (U.S. Pat. No. 6,180,373 B1), *E. coli* AGX17 (pGX44) (NRRL B-12263) and AGX6(pGX50)aroP (NRRL B-12264) deficient in the enzyme tryptophanase (U.S. Pat. No. 4,371,614), *E. coli* AGX17/pGX50, pACKG4-pps having an enhanced phosphoenolpyruvate-producing ability (WO97/08333, U.S. Pat. No. 6,319,696 B1), and the like. Examples of L-tryptophan-producing bacteria and parental strains which can be used to derive the L-tryptophan-producing bacteria also include strains belonging to the genus *Escherichia* and having an enhanced activity of the protein encoded by and the yedA gene or the yddG gene (U.S. Patent Application Nos. 2003148473 A1 and 2003157667 A1).

Examples of L-tryptophan-producing bacteria and parental strains which can be used to derive the L-tryptophan-producing bacteria also include strains in which one or more activities of the enzymes selected from anthranilate synthase, phosphoglycerate dehydrogenase, and tryptophan synthase are enhanced. The anthranilate synthase and phosphoglycerate dehydrogenase are both subject to feedback inhibition by L-tryptophan and L-serine, and hence, a mutation desensitizing the feedback inhibition may be introduced into these enzymes. Specific examples of strains having such a mutation include *E. coli* SV164, which harbors desensitized anthranilate synthase, and a transformant strain obtained by introducing into the *E. coli* SV164 the plasmid pGH5 (WO94/08031 A1), which contains a mutant serA gene encoding feedback-desensitized phosphoglycerate dehydrogenase.

Examples of L-tryptophan-producing bacteria and parental strains which can be used to derive the L-tryptophan-producing bacteria also include strains into which the tryptophan operon which contains a gene encoding desensitized anthranilate synthase has been introduced (JP 57-71397 A, JP 62-244382 A, U.S. Pat. No. 4,371,614). Moreover, L-tryptophan-producing ability may be imparted by enhancing expression of a gene which encodes tryptophan synthase, among tryptophan operons (trpBA). The tryptophan synthase consists of α and β subunits which are encoded by the trpA and trpB genes, respectively. In addition, L-tryptophan-producing ability may be improved by enhancing expression of the isocitrate lyase-malate synthase operon (WO2005/103275).

L-Valine-Producing Bacteria

Examples of L-valine-producing bacteria and parental strains which can be used to derive L-valine-producing bacteria include, but are not limited to, strains which have been modified to overexpress the ilvGMEDA operon (U.S. Pat. No. 5,998,178). It is desirable to remove the region of the ilvGMEDA operon which is required for attenuation so that expression of the operon is not attenuated by the L-valine that is produced. Furthermore, the ilvA gene in the operon is desirably disrupted so that threonine deaminase activity is decreased.

Examples of L-valine-producing bacteria and parental strains for deriving L-valine-producing bacteria also include mutant strains having a mutation in aminoacyl-tRNA synthetase (U.S. Pat. No. 5,658,766). Examples of such strains include E. coli VL1970, which has a mutation in the ileS gene encoding isoleucine tRNA synthetase. E. coli VL1970 was deposited in the Russian National Collection of Industrial Microorganisms (VKPM; Russian Federation, 117545 Moscow, 1$^{st}$ Dorozhny proezd, 1) on Jun. 24, 1988 under the accession number VKPM B-4411.

Furthermore, mutant strains requiring lipoic acid for growth and/or lacking H$^+$-ATPase can also be used as L-valine-producing bacteria or parental strains thereof (WO96/06926 A1).

Examples of L-valine-producing bacteria and parent strains for deriving L-valine-producing bacteria also include E. coli H81 strain (VKPM B-8066; see, for example, EP1942183 B1), E. coli NRRL B-12287 and NRRL B-12288 (U.S. Pat. No. 4,391,907), E. coli VKPM B-4411 (U.S. Pat. No. 5,658,766), E. coli VKPM B-7707 (EP1016710 A2), or the like.

The bacterium of the present invention belonging to the family Enterobacteriaceae has been modified to attenuate expression of the gshA gene.

The phrase "gshA gene" can mean a gene which encodes an enzyme having an activity of γ-glutamate-cysteine ligase. A specific example of the gene which encodes the enzyme having the activity of γ-glutamate-cysteine ligase includes the gshA gene which encodes γ-glutamate-cysteine ligase. The gene encoding the enzyme having the activity of γ-glutamate-cysteine ligase can be the gshA gene. The more specific description of gshA gene is given hereinafter.

The gshA gene (synonym: gsh-1) encodes γ-glutamate-cysteine ligase GshA (synonym: γ-glutamylcysteine synthetase, γGCS) (KEGG, Kyoto Encyclopedia of Genes and Genomes, entry No. b2688; Protein Knowledgebase, UniProtKB/Swiss-Prot, accession No. P0A6W9). The gshA gene (GenBank, accession No. NC_000913.3; nucleotide positions: 2814883 to 2816439, complement; Gene ID: 944881) is located between the yqaA gene on the same strand and the micA gene on the opposite strand on the chromosome of E. coli strain K-12. The nucleotide sequence of the gshA gene (SEQ ID NO: 1) of E. coli strain K-12 and the amino acid sequence of the γGCS protein (SEQ ID NO: 2) encoded by the gshA gene of E. coli strain K-12 are known. That is, the gshA gene may have the nucleotide sequence of SEQ ID NO: 1, and the γGCS protein encoded by the gshA gene may have the amino acid sequence of SEQ ID NO: 2. The phrase "a gene or protein has a nucleotide or amino acid sequence" encompasses cases where a gene or protein includes the nucleotide or amino acid sequence, and cases where a gene or protein consists of the nucleotide or amino acid sequence.

The phrase "a bacterium has been modified to attenuate expression of the gshA gene" can mean that the bacterium has been modified in such a way that in the modified bacterium expression of the gshA gene is attenuated. The phrase "a bacterium has been modified to attenuate expression of the gshA gene" can specifically mean that the bacterium has been modified in such a way that in the modified bacterium expression of the gshA gene is attenuated as compared with a non-modified bacterium. Exemplary, the expression of the gshA gene can be attenuated due to inactivation of the gshA gene.

The phrase "the gshA gene is inactivated" can mean that the modified gene encodes a completely inactive or non-functional protein, i.e. completely inactive or non-functional γ-glutamate-cysteine ligase. It is also acceptable that the modified DNA region is unable to naturally express the gene due to deletion of a part of the gene or deletion of the entire gene, replacement of one base or more to cause an amino acid substitution in the protein encoded by the gene (missense mutation), introduction of a stop codon (nonsense mutation), deletion of one or two bases to cause a reading frame shift of the gene, insertion of a drug-resistance gene and/or transcription termination signal, or modification of an adjacent region of the gene, including sequences controlling gene expression such as promoter(s), enhancer(s), attenuator(s), ribosome-binding site(s), etc. Inactivation of the gene can also be performed, for example, by conventional methods such as a mutagenesis treatment using UV irradiation or nitrosoguanidine (N-methyl-N'-nitro-N-nitrosoguanidine), site-directed mutagenesis, gene disruption using homologous recombination, and/or insertion-deletion mutagenesis (Yu D. et al., Proc. Natl. Acad. Sci. USA, 2000, 97(11):5978-5983; Datsenko K. A. and Wanner B. L., Proc. Natl. Acad. Sci. USA, 2000, 97(12):6640-6645; Zhang Y. et al., Nature Genet., 1998, 20:123-128) based on "Red/ET-driven integration" or "λRed/ET-mediated integration".

The phrase "expression of the gshA gene is attenuated" can also mean that the modified bacterium contains a region operably linked to the gshA gene, including sequences controlling gene expression such as promoters, enhancers, attenuators and transcription termination signals, ribosome-binding sites, and other expression control elements, which is modified resulting in the decrease of the expression level of the gshA gene; and other examples (see, for example, WO95/34672; Carrier T. A. and Keasling J. D., Biotechnol. Prog., 1999, 15:58-64). The phrase "operably linked to the gene" can mean that the regulatory region(s) is/are linked to the nucleotide sequence of the nucleic acid molecule or gene in such a manner which allows for expression (e.g., enhanced, increased, constitutive, basal, antiterminated, attenuated, deregulated, decreased, or repressed expression) of the nucleotide sequence, specifically, the expression of a gene product encoded by the nucleotide sequence.

The phrase "expression of the gshA gene is attenuated" can also mean that the amount of the expression product of the gshA gene, such as the amount of mRNA of the gene or the amount of the γGCS protein encoded by the gene, in the modified bacterium, in which expression of the gshA gene is attenuated, is reduced to, for example, 50% or less, 20% or less, 10% or less, 5% or less, or 0% of that in a non-modified bacterium.

The phrase "a bacterium has been modified to attenuate expression of the gshA gene" can also mean that the bacterium has been modified in such a way that in the modified bacterium the total enzymatic activity of the gshA gene product such as γGCS protein is decreased as compared with a non-modified bacterium. The bacterium can be modified so that the activity of the γGCS protein per cell is decreased to, for example, 50% or less, 20% or less, 10% or less, 5% or less, or 0% of that in a non-modified bacterium.

Examples of a non-modified bacterium serving as a reference for the above comparisons can include wild-type strains of a bacterium belonging to the genus Escherichia, such as the E. coli MG1655 strain (ATCC 47076) and E. coli W3110 strain (ATCC 27325), or a bacterium belonging to the genus Pantoea, such as the P. ananatis AJ13355 strain (FERM BP-6614), and so forth. Examples of a non-modified bacterium serving as a reference for the above comparisons can also include a parental strain which has not been modified to attenuate expression of the gshA gene or a bacterium in which expression of the gshA gene is not attenuated.

The phrase "activity of γ-glutamate-cysteine ligase" can mean the enzymatic activity of catalyzing the following reaction (EC number: 6.3.2.2): L-cysteine+L-glutamate+ ATP ↔ γ-L-glutamyl-L-cysteine+ADP+phosphate+H+, where ATP can mean adenosine triphosphate and ADP can mean adenosine diphosphate.

The enzymatic activity of γ-glutamate-cysteine ligase can be determined by evaluating adenosine diphosphate (ADP) formation using a pyruvate kinase-lactate dehydrogenase-coupled assay (Seelig G. F. and Meister A., Glutathione biosynthesis; gamma-glutamylcysteine synthetase from rat kidney, *Methods Enzymol.*, 1985; 113:379-390) or dipeptide formation using L-α-[$^{14}$C]aminobutyrate (Griffith O. W. and Meister A., Selective inhibition of gamma-glutamyl-cycle enzymes by substrate analogs, *Proc. Natl. Acad. Sci. USA*, 1977, 74(8):3330-3334). The direct measuring of γ-glutamylcysteine by high-performance liquid chromatography and electrochemical detection may also be used (Gegg M. E. et al., Determination of glutamate-cysteine ligase (gamma-glutamylcysteine synthetase) activity by high-performance liquid chromatography and electrochemical detection, *Anal. Biochem.*, 2002, 304(1):26-32). The protein concentration can be determined by the Bradford protein assay using bovine serum albumin as a standard (Bradford M. M., *Anal. Biochem.*, 1976, 72:248-254).

Expression of the gshA gene can be attenuated by replacing an expression control sequence of the gene, such as a promoter on the chromosomal DNA, with a weaker one. The strength of a promoter is defined by the frequency of initiation acts of RNA synthesis. Examples of methods for evaluating the strength of promoters and strong promoters are described in Goldstein M. A. et al. (Goldstein M. A. and Doi R. H., Prokaryotic promoters in biotechnology, *Biotechnol. Anna. Rev.*, 1995, 1:105-128), and so forth. Furthermore, it is also possible to introduce one or more nucleotide substitutions in a promoter region of the gene and thereby modify the promoter to be weakened as disclosed in WO0018935 A1. Furthermore, it is known that substitution of several nucleotides in the Shine-Dalgarno (SD) sequence, and/or in the spacer between the SD sequence and the start codon, and/or a sequence immediately upstream and/or downstream from the start codon in the ribosome-binding site (RBS) greatly affects the translation efficiency of mRNA. This modification of such a region may be combined with decreasing transcription of the gshA gene.

Expression of the gshA gene can also be attenuated by inserting a transposon or an insertion sequence (IS) into the coding region of the gene (U.S. Pat. No. 5,175,107) or in the region controlling gene expression, or by conventional methods such as mutagenesis with ultraviolet (UV) irradiation or nitrosoguanidine (N-methyl-N'-nitro-N-nitrosoguanidine, NTG). Furthermore, the incorporation of a site-specific mutation can be conducted by known chromosomal editing methods based, for example, on λRed/ET-mediated recombination (Datsenko K. A. and Wanner B. L., *Proc. Natl. Acad. Sci. USA*, 2000, 97(12):6640-6645).

The copy number, presence or absence of the gshA gene can be measured, for example, by restricting the chromosomal DNA followed by Southern blotting using a probe based on the gene sequence, fluorescence in situ hybridization (FISH), and the like. The level of gene expression can be determined by measuring the amount of mRNA transcribed from the gene using various well-known methods, including Northern blotting, quantitative RT-PCR, and the like. The amount of the protein encoded by the gene can be measured by known methods including SDS-PAGE followed by immunoblotting assay (Western blotting analysis), or mass spectrometry analysis of the protein samples, and the like.

Methods for manipulation with recombinant molecules of DNA and molecular cloning such as preparation of plasmid DNA, digestion, ligation and transformation of DNA, selection of an oligonucleotide as a primer, incorporation of mutations, and the like may be ordinary methods well-known to the person skilled in the art. These methods are described, for example, in Sambrook J., Fritsch E. F. and Maniatis T., "Molecular Cloning: A Laboratory Manual", $2^{nd}$ ed., Cold Spring Harbor Laboratory Press (1989) or Green M. R. and Sambrook J. R., "Molecular Cloning: A Laboratory Manual", $4^{th}$ ed., Cold Spring Harbor Laboratory Press (2012); Bernard R. Glick, Jack J. Pasternak and Cheryl L. Patten, "Molecular Biotechnology: principles and applications of recombinant DNA", $4^{th}$ ed., Washington, D.C., ASM Press (2009).

There may be some differences in DNA sequences between the genera, species, or strains of the family Enterobacteriaceae. Therefore, the gshA gene is not limited to the gene shown in SEQ ID NO: 1, but may include genes which are variant nucleotide sequences of SEQ ID NO: 1, and which encode the γGCS protein. That is, the phrase "the gshA gene" is not limited to the gshA gene shown in SEQ ID NO: 1, but can correctively refer to the gshA gene shown in SEQ ID NO: 1 and variant nucleotide sequences thereof.

Similarly, the phrase "the γGCS" or "the γGCS protein" is not limited to the γGCS protein shown in SEQ ID NO: 2, but can correctively refer to the γGCS protein shown in SEQ ID NO: 2 and variant proteins thereof.

The phrase "a variant protein" can mean a protein which has one or more mutations in the sequence compared with SEQ ID NO: 2, whether they are substitutions, deletions, insertions, and/or additions of one or several amino acid residues, but which still maintains an activity or function similar to that of the γGCS protein, such as the activity of γ-glutamate-cysteine ligase as described above, or of which the three-dimensional structure is not significantly changed relative to the wild-type protein. The number of changes in the variant protein depends on the position of amino acid residues in the three-dimensional structure of the protein or the type of amino acid residues. It can be, but is not strictly limited to, 1 to 100, in another example 1 to 50, in another example 1 to 30, in another example 1 to 15, in another example 1 to 10, and in another example 1 to 5, in SEQ ID NO: 2. This is because some amino acids have high homology to one another, so that the activity or function of a protein is not affected by a change between such amino acids, or the three-dimensional structure of a protein is not significantly changed relative to the wild-type protein by a change between such amino acids. Therefore, the variant proteins encoded by the gshA gene may have a homology, defined as the parameter "identity" when using the computer program BLAST, of not less than 65%, not less than 70%, not less than 75%, not less than 80%, not less than 85%, not less than 90%, not less than 95%, not less than 98%, or not less than 99% with respect to the entire amino acid sequence shown in SEQ ID NO: 2, as long as the activity or function of the γGCS protein is maintained, or the three-dimensional structure of γGCS protein is not significantly changed relative to the wild-type γGCS protein.

The exemplary substitution, deletion, insertion, and/or addition of one or several amino acid residues can be a conservative mutation(s). The representative conservative mutation is a conservative substitution. The conservative substitution can be, but is not limited to, a substitution, wherein substitution takes place mutually among Phe, Trp and Tyr, if the substitution site is an aromatic amino acid; among Ala, Leu, Ile and Val, if the substitution site is a hydrophobic amino acid; between Glu, Asp, Gln, Asn, Ser, His and Thr, if the substitution site is a hydrophilic amino acid; between Gln and Asn, if the substitution site is a polar amino acid; among Lys, Arg and His, if the substitution site is a basic amino acid; between Asp and Glu, if the substitution site is an acidic amino acid; and between Ser and Thr, if the substitution site is an amino acid having hydroxyl group. Examples of conservative substitutions include substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val.

The exemplary substitution, deletion, insertion, and/or addition of one or several amino acid residues can also be a non-conservative mutation(s) provided that the mutation(s) is/are compensated by one or more secondary mutations in the different position(s) of amino acids sequence so that the activity or function similar to that of the γGCS protein, such as the activity of γ-glutamate-cysteine ligase as described above, is maintained, or the three-dimensional structure of γGCS protein is not significantly changed relative to the wild-type γGCS protein.

To evaluate the degree of protein or DNA homology, several calculation methods can be used, such as BLAST search, FASTA search and ClustalW method. The BLAST (Basic Local Alignment Search Tool, www.ncbi.nlm.nih.gov/BLAST/) search is the heuristic search algorithm employed by the programs blastp, blastn, blastx, megablast, tblastn, and tblastx; these programs ascribe significance to their findings using the statistical methods of Karlin S. and Altschul S. F. (Methods for assessing the statistical significance of molecular sequence features by using general scoring schemes, *Proc. Natl. Acad. Sci. USA,* 1990, 87:2264-2268; Applications and statistics for multiple high-scoring segments in molecular sequences, *Proc. Natl. Acad. Sci. USA,* 1993, 90:5873-5877). The computer program BLAST calculates three parameters: score, identity and similarity. The FASTA search method is described by Pearson W. R. (Rapid and sensitive sequence comparison with FASTP and FASTA, *Methods Enzymol.,* 1990, 183:63-98). The ClustalW method is described by Thompson J. D. et al. (CLUSTAL W: improving the sensitivity of progressive multiple sequence alignment through sequence weighting, position-specific gap penalties and weight matrix choice, *Nucleic Acids Res.,* 1994, 22:4673-4680).

Examples of variant proteins of the γGCS protein shown in SEQ ID NO: 2 can include protein homologues of γGCS (γGCS homologues) from different bacteria of the family Enterobacteriaceae. That is, γGCS homologues from different bacteria of the family Enterobacteriaceae are known, that have the activity of γ-glutamate-cysteine ligase as described above. Examples of such γGCS homologues from the bacteria belonging to the family Enterobacteriaceae are described hereinafter (Table 1) with indication of a homology value (as "identity", that is the identity of amino acids), taxonomy data, and accession and sequence record numbers of amino acid sequences in the NCBI database (National Center for Biotechnology Information, ncbi.nlm.nih.gov/protein).

TABLE 1

| Identity | Organism | Accession No.*; Sequence record (GI) No.* |
|---|---|---|
| 100% | *Escherichia coli* (strain K-12) | NP_417173.1; GI: 16130600 |
| 87% | *Klebsiella pneumoniae* | CDO12865.1; GI: 597513774 |
| 99% | *Shigella sonnei* | WP_000611798.1; GI: 446534452 |
| 94% | *Salmonella enterica* | WP_000611815.1; GI: 446534469 |
| 87% | *Enterobacter aerogenes* | WP_032712382.1; GI: 695798191 |
| 67% | *Pantoea ananatis* (strain AJ13355) | BAK12383.1; GI: 327394961 |
| 87% | *Klebsiella pneumoniae* | KGZ19147.1; GI: 721575847 |
| 73% | *Pantoea* sp. IMH | WP_033758687.1; GI: 727301739 |
| 68% | *Erwinia amylovora* (strain ATCC BAA-2158) | CBX79664.1; GI: 312171405 |
| 76% | *Serratia liquefaciens* | WP_044554246.1; GI: 764987737 |
| 99% | *Shigella flexneri* | WP_000611805.1; GI: 446534459 |
| 68% | *Morganella morganii* | WP_036426159.1; GI: 738475870 |
| 73% | *Dickeya dadantii* | WP_013319093.1; GI: 503084223 |

*in the NCBI database (National Center for Biotechnology Information, ncbi.nlm.nih.gov)

The gshA gene can be any gene encoding the γGCS protein. For example, the gshA gene can be a variant nucleotide sequence. The phrase "a variant nucleotide sequence" can mean a nucleotide sequence which encodes "a variant protein" as described above, or a nucleotide sequence which encodes any wild-type γGCS protein such as the γGCS protein shown in SEQ ID NO: 2 using any synonymous amino acid codons according to the standard genetic code table (see, e.g., Lewin B., "Genes VIII", 2004, Pearson Education, Inc., Upper Saddle River, N.J. 07458). Therefore, the gshA gene can be a variant nucleotide sequence due to the degeneracy of the genetic code such as a variant nucleotide sequence of SEQ ID NO: 1 due to the degeneracy of the genetic code.

The phrase "a variant nucleotide sequence" can also mean, but is not limited to, a nucleotide sequence which hybridizes under stringent conditions with the nucleotide sequence complementary to the sequence shown in SEQ ID NO: 1 or a probe which can be prepared from the nucleotide sequence under stringent conditions provided that it encodes a functional protein. "Stringent conditions" include those under which a specific hybrid, for example, a hybrid having homology, defined as the parameter "identity" when using the computer program BLAST, of not less than 60%, not less than 65%, not less than 70%, not less than 75%, not less than 80%, not less than 85%, not less than 90%, not less than 95%, not less than 96%, not less than 97%, not less than 98%, or not less than 99% is formed, and a non-specific hybrid, for example, a hybrid having homology lower than the above is not formed. For example, stringent conditions can be exemplified by washing one time or more, or in another example, two or three times, at a salt concentration of 1×SSC (standard sodium citrate or standard sodium chloride), 0.1% SDS (sodium dodecyl sulphate), or in another example, 0.1×SSC, 0.1% SDS at 60° C. or 65° C. Duration of washing depends on the type of membrane used for blotting and, as a rule, can be what is recommended by the manufacturer. For example, the recommended duration of washing for the Amersham Hybond™-N+ positively charged nylon membrane (GE Healthcare) under stringent conditions is 15 minutes. The washing step can be performed 2 to 3 times. As the probe, a part of the sequence complementary to the sequence shown in SEQ ID NO: 1 may also be used. Such a probe can be produced by PCR using oligonucleotides as primers prepared on the basis of the sequence shown in SEQ ID NO: 1 and a DNA-fragment containing the nucleotide sequence as a template. The length of the probe is recommended to be >50 bp; it can be suitably selected depending on the hybridization conditions, and is usually 100 bp to 1 kbp. For example, when a DNA-fragment having a length of about 300 bp is used as the probe, the washing conditions after hybridization can be exemplified by 2×SSC, 0.1% SDS at 50° C., 60° C. or 65° C.

As the gene encoding the γGCS protein of the species *E. coli* has already been elucidated (see above), the variant nucleotide sequences encoding the γGCS protein can be obtained by PCR (polymerase chain reaction; refer to White T. J. et al., The polymerase chain reaction, *Trends Genet.*, 1989, 5:185-189) utilizing primers prepared based on the nucleotide sequence of the gshA gene; or the site-directed mutagenesis method by treating a DNA containing the wild-type gshA gene in vitro, for example, with hydroxylamine, or a method for treating a microorganism, for example, a bacterium belonging to the family Enterobacteriaceae harboring the wild-type gshA gene with ultraviolet (UV) irradiation or a mutating agent such as N-methyl-N'-nitro-N-nitrosoguanidine (NTG) and nitrous acid usually used for the such treatment; or chemically synthesized as full-length gene structure. That is, genes encoding the γGCS protein of other bacteria of the family Enterobacteriaceae can be thus obtained.

The phrase "a wild-type protein" can mean a native protein naturally produced by a wild-type or parent bacterial strain of the family Enterobacteriaceae, for example, by the wild-type *E. coli* MG1655 strain. A wild-type protein can be encoded by the "wild-type gene", which can be present in genome of a wild-type bacterium.

The above descriptions concerning variants of the genes and proteins can also be applied mutatis mutandis to arbitrary proteins such as L-amino acid biosynthesis enzymes and genes coding for them.

The bacterium can have, in addition to the properties already mentioned, other specific properties such as various nutrient requirements, drug resistance, drug sensitivity, and drug dependence, without departing from the scope of the present invention.

2. Method

A method of the present invention includes the method for producing an L-amino acid such as L-alanine, L-arginine, L-asparagine, L-aspartic acid, L-citrulline, L-cysteine, L-glutamic acid, L-glutamine, glycine, L-histidine, L-isoleucine, L-leucine, L-lysine, L-methionine, L-ornithine, L-phenylalanine, L-proline, L-serine, L-threonine, L-tryptophan, L-tyrosine, and L-valine, or a mixture thereof. Specifically, a method of the present invention includes the method for producing branched-chain L-amino acids, such as L-isoleucine, L-leucine, and L-valine, or a mixture thereof. More specifically, a method of the present invention includes the method for producing L-valine.

The method for producing an L-amino acid can include the steps of cultivating the bacterium as described herein in a culture medium to allow the L-amino acid to be produced, excreted, and/or accumulated in the culture medium or in the bacterium (i.e. the bacterial cells), or both, and collecting the L-amino acid from the culture medium and/or the bacterium (i.e. the bacterial cells). Collected amino acid can be further purified. The target L-amino acid can be produced in a free form, a salt form or a hydrate form thereof, or an adduct form thereof with another organic or inorganic compound, or as a combination thereof. That is, the phrase "L-amino acid" may refer to an L-amino acid in a free form, a salt form thereof, a hydrate form thereof, an adduct form thereof, or a mixture thereof. Also, the phrase "L-amino acid" may specifically refer to an L-amino acid in a free form, a salt form thereof, or a mixture thereof. For example, ammonium, sodium, potassium, and the like salts or an inner salt such as zwitterion of the L-amino acid can be produced by the method. This is possible as amino acids can react under fermentation conditions with each other or a neutralizing agent such as an inorganic or organic acidic or alkaline substance in a typical acid-base neutralization reaction to form a salt that is the chemical feature of amino acids which is apparent to one skilled in the art. Specifically, a monochlorhydrate salt of an L-amino acid can be produced by the method such as monochlorhydrate salt of L-lysine (L-lysine-HCl) or monochlorhydrate salt of L-arginine (L-arginine-HCl); or monochlorhydrate salt monohydrate of an L-amino acid can be produced by the method such as monochlorhydrate monohydrate of L-histidine (L-histidine-HCl.H$_2$O).

The cultivation of the bacterium, and collection and purification of L-amino acids may be performed in a manner similar to conventional fermentation methods wherein an L-amino acid is produced using a microorganism. The culture medium for production of the L-amino acid can be either a synthetic or natural medium such as a typical medium that contains a carbon source, a nitrogen source, a sulphur source, phosphorous source, inorganic ions, and other organic and inorganic components as required. As the carbon source, saccharides such as glucose, lactose, galactose, fructose, arabinose, maltose, xylose, trehalose, ribose, sucrose, and hydrolysates of starches; alcohols such as ethanol, glycerol, mannitol, and sorbitol; organic acids such as gluconic acid, fumaric acid, citric acid, malic acid, and succinic acid; fatty acids; and the like can be used. As the nitrogen source, inorganic ammonium salts such as ammonium sulfate, ammonium chloride, and ammonium phosphate; organic nitrogen such as of soy bean hydrolyzates; ammonia gas; aqueous ammonia; and the like can be used. Furthermore, peptone, yeast extract, meat extract, malt extract, corn steep liquor, and so forth can also be utilized. The sulphur source can include ammonium sulphate, magnesium sulphate, ferrous sulphate, manganese sulphate, and the like. The medium can contain a phosphorus source in addition to the carbon source, the nitrogen source, and the sulphur source. As the phosphorus source, potassium dihydrogen phosphate, dipotassium hydrogen phosphate, phosphate polymers such as pyrophosphoric acid and so forth can be utilized. Vitamins such as vitamin B1, vitamin B2, vitamin B6, nicotinic acid, nicotinamide, and vitamin B12; required substances, for example, organic nutrients such as nucleic acids such as adenine and RNA, amino acids, peptone, casamino acid, or yeast extract; and the like may be present in appropriate, even if trace, amounts. Other than these, small amounts of calcium phosphate, iron ions, manganese ions, and the like may be added, if necessary.

Cultivation can be performed under aerobic conditions for 16 to 72 h, or for 16 to 65 h; the culture temperature during cultivation can be controlled within 30 to 45° C., or within 30 to 37° C.; and the pH can be adjusted between 5 and 8, or between 6.0 and 7.5. The pH can be adjusted by using an inorganic or organic acidic or alkaline substance, as well as ammonia gas.

After cultivation, the target L-amino acid can be collected from the culture medium. Also, after cultivation, the cells can be disrupted with, for example, supersonic waves or the like, the supernatant can be obtained by removing solids such as the cells and the cell-disrupted suspension (also referred to as cell debris) by, for example, centrifugation or membrane filtration, and then the target L-amino acid can be collected from the supernatant. Collection of L-amino acid from the culture medium or the supernatant etc can be performed by any combination of conventional techniques such as concentration, ion-exchange chromatography, and crystallization.

The collected target L-amino acid composition may contain microbial cells, medium components, moisture, and by-product metabolites of the microorganism in addition to the target L-amino acid. Purity of the collected target L-amino acid can be 50% or higher, preferably 85% or higher, particularly preferably 95% or higher (U.S. Pat. No. 5,431,933, Japanese Patent No. 1214636, U.S. Pat. Nos. 4,956,471, 4,777,051, 4,946,654, 5,840,358, 6,238,714, U.S. Patent Published Application No. 2005/0025878).

EXAMPLES

The present invention will be more specifically explained below with reference to the following non-limiting examples.

Example 1

Construction of the E. coli Strain Having an Inactivated gshA Gene 1.1. Construction of E. coli MG1655ΔgshA Strain An E. coli strain having an inactivated gshA gene was constructed by the method initially developed by Datsenko K. A. and Wanner B. L. called "λRed/ET-mediated integration" (Datsenko K. A. and Wanner B. L., Proc. Natl. Acad. Sci. USA, 2000, 97(12):6640-6645). According to this method, the PCR-primers P1 (SEQ ID NO: 3) and P2 (SEQ ID NO: 4), each of which is homologous to a region adjacent to the gshA gene at either end, and a region adjacent to the cat gene conferring chloramphenicol resistance ($Cm^R$) in the template plasmid at the other end, were constructed. The plasmid pMIV-5JS (JP2008-99668, EP1942183 A1) was used as the template. Conditions for PCR were as follows: denaturation for 3 min at 95° C.; profile for the initial 2 cycles: 1 min at 95° C., 30 sec at 34° C., 1 min at 72° C.; profile for the final 30 cycles: 30 sec at 95° C., 30 sec at 50° C., 1 min at 72° C.; final elongation: 5 min at 72° C.

The obtained PCR-product 1 (SEQ ID NO: 5; 1,378 bp) was purified by electrophoresis in agarose gel and used for electroporation of the E. coli MG1655 strain containing the pKD46 plasmid having a temperature-sensitive replication origin. The pKD46 plasmid (Datsenko K. A. and Wanner B. L., Proc. Natl. Acad. Sci. USA, 2000, 97(12):6640-6645) includes a 2,154 nucleotides DNA-fragment of phage λ (nucleotide positions from 31088 to 33241; GenBank, accession No. J02459), and thus contains genes of the λRed homologous recombination system (γ, β, and exo genes) under the control of the arabinose-inducible $P_{araB}$ promoter. The pKD46 plasmid is necessary for integration of the PCR-product into the chromosome of the E. coli MG1655 strain (ATCC 47076). The E. coli MG1655 strain containing the pKD46 plasmid can be obtained from the E. coli Genetic Stock Center, Yale University, New Haven, USA (Accession No. CGSC7669).

Electrocompetent cells were prepared as follows: E. coli MG1655/pKD46 was grown overnight at 30° C. in LB-medium (Luria-Bertani broth, also referred to as lysogenic broth; Sambrook J. and Russell D. W., Molecular Cloning: A Laboratory Manual ($3^{rd}$ ed.), Cold Spring Harbor Laboratory Press, 2001) containing ampicillin (100 mg/L); then the culture was diluted 100 times with 5 mL of SOB-medium (Sambrook J., Fritsch E. F. and Maniatis T., Molecular Cloning: A Laboratory Manual ($2^{nd}$ ed.), Cold Spring Harbor Laboratory Press, 1989) containing ampicillin (100 mg/L) and L-arabinose (1 mM). The diluted culture was grown with aeration (250 rpm) at 30° C. to $OD_{600}$ of about 0.6 and then made electrocompetent by concentrating 100-fold and washing three times with ice-cold deionized $H_2O$. Electroporation was performed using 70 μL of cells and about 100 ng of the PCR-product 1. Electroporated cells were incubated with 1 mL of SOC-medium (Sambrook J. et al., Molecular Cloning: A Laboratory Manual ($2^{nd}$ ed.), Cold Spring Harbor Laboratory Press, 1989) at 37° C. for 2.5 hours, placed onto the plates containing the lysogenic broth (Sambrook J. and Russell D. W., Molecular Cloning: A Laboratory Manual ($3^{rd}$ ed.), Cold Spring Harbor Laboratory Press, 2001), agar (1.5%) and chloramphenicol (10 mg/L), and grown at 37° C. to select $Cm^R$-recombinants. To eliminate the pKD46 plasmid, two passages on L-agar supplemented with chloramphenicol (10 mg/L) at 42° C. were performed, and the obtained colonies were tested for sensitivity to ampicillin. Thus the E. coli MG1655ΔgshA strain having the $Cm^R$-marker, which is also referred to as the E. coli MG1655ΔgshA::$Cm^R$ strain, was obtained.

1.2. Verification of Deletion of the gshA Gene

The deletion of gshA gene marked with chloramphenicol resistance gene (cat) in the mutant E. coli MG1655ΔgshA strain was verified by PCR. Locus-specific primers P3 (SEQ ID NO: 6) and P4 (SEQ ID NO: 7) were used for the verification. Conditions for PCR were as follows: denaturation for 3 min at 94° C.; profile for the 30 cycles: 30 sec at 94° C., 30 sec at 58° C., 2 min at 72° C.; final elongation: 6 min at 72° C. The PCR-product 2, obtained in the reaction with the chromosomal DNA as the template from the parental E. coli MG1655 having native gshA gene, was 2,155 bp in length (SEQ ID NO: 8). The PCR-product 3, obtained in the reaction with the chromosomal DNA as a template from the mutant E. coli MG1655ΔgshA::$Cm^R$, was 1,858 bp in length (SEQ ID NO: 9).

Example 2

Construction of the E. coli L-Valine-Producing Strain Having an Inactivated gshA Gene To test the effect from inactivation of the gshA gene on L-valine production, the DNA-fragments from the chromosome of the above-described E. coli MG1655ΔgshA::$Cm^R$ strain (Example 1.1) were transferred to the valine-producing E. coli strain H81 by P1-transduction (Miller J. H., Experiments in Molecular Genetics, Cold Spring Harbor Lab. Press, Plainview, N.Y., 1972) to obtain the strain E. coli H81ΔgshA::Cm$^R$. The strain H81 (EP1239041 A2) was deposited in the Russian National Collection of Industrial Microorganisms (VKPM; FGUP GosNII Genetika, Russian Federation, 117545 Moscow, 1$^{st}$ Dorozhny proezd, 1) on Jan. 30, 2001 under the accession number VKPM B-8066 and then converted to an international deposit under the provisions of the Budapest Treaty on Feb. 1, 2002. The *E. coli* H81 strain having the inactivated gshA gene was selected on the plates containing the lysogenic broth, agar (1.5%) and chloramphenicol (10 mg/L). Thus the *E. coli* H81ΔgshA::Cm$^R$ strain was obtained. The deletion of gshA marked with chloramphenicol resistance gene was verified by PCR as described in Example 1.2.

Example 3

Production of L-Valine by *E. coli* H81ΔgshA::Cm$^R$ Strain

The modified *E. coli* H81ΔgshA::Cm$^R$ and the control *E. coli* H81 strains were separately cultivated in 2 mL of LB-medium for 18 hours at 34° C. Then, 0.2 mL of obtained cultures were each inoculated into 2 mL of fermentation medium in 20×200-mm test tubes and cultivated for 72 hours at 34° C. on a rotary shaker (250 rpm) until glucose consumption.

The composition of the fermentation medium (g/L) was as follows:

| | |
|---|---|
| Glucose | 76.0 |
| (NH$_4$)$_2$SO$_4$ | 18.0 |
| KH$_2$PO$_4$ | 1.8 |
| MgSO$_4$•7H$_2$O | 1.2 |
| Thiamine-HCl | 0.1 |
| CaCO$_3$ | 24.0 |
| LB-medium | 10% (v/v) |

The fermentation medium was sterilized at 116° C. for 30 min. Glucose and CaCO$_3$ were sterilized separately as follows: glucose at 110° C. for 30 min and CaCO$_3$ at 116° C. for 30 min. The pH was adjusted to 7.0 by 6M KOH before sterilization.

After the cultivation, the amount of L-valine, which accumulated in the medium, was determined by thin layer chromatography (TLC). The 10×20-cm TLC plates coated with Merck silica gel 60 without fluorescent indicator (Merck, Darmstadt, Germany) were used. Samples were applied onto the plates using the Camag Linomat 5 sample applicator. The Merck plates were developed with a mobile phase consisting of propan-2-ol:ethyl acetate:25% aqueous ammonia:water=16:16:5:10 (v/v). A solution of ninhydrin (2%, w/v) in acetone was used as a visualizing reagent. After development, plates were dried and scanned with the Camag TLC Scanner 3 in absorbance mode with detection at 520 nm using winCATS software (version 1.4.2).

The results of four independent test-tube fermentations (as average values) are shown in Table 2. As it can be seen from the Table 2, the modified *E. coli* H81ΔgshA::Cm$^R$ strain was able to produce a higher amount (g/L) of L-valine (Val) as compared with the parent *E. coli* H81 strain. Table 2 also shows that the modified *E. coli* H81ΔgshA::Cm$^R$ strain was able to produce L-valine with higher yield (%, relative to consumed glucose) as compared with the parent *E. coli* H81 strain.

TABLE 2

| Strain | OD$_{600}$ | Val, g/L | Val yield, % |
|---|---|---|---|
| *E. coli* H81 (control) | 32 ± 2 | 7.1 ± 0.5 | 9.3 ± 0.7 |
| *E. coli* H81ΔgshA::Cm$^R$ | 28 ± 1 | 8.4 ± 0.5 | 11.0 ± 0.7 |

Example 4

Production of L-Arginine by *E. coli* 382ΔgshA Strain

To test the effect from inactivation of the gshA gene on L-arginine production, the DNA-fragments from the chromosome of the above-described *E. coli* MG1655ΔgshA::Cm$^R$ are transferred to the arginine-producing *E. coli* strain 382 by P1-transduction to obtain the strain *E. coli* 382ΔgshA. The strain 382 was deposited in the Russian National Collection of Industrial Microorganisms (VKPM; FGUP GosNII Genetika, Russian Federation, 117545 Moscow, 1$^{st}$ Dorozhny proezd, 1) on Apr. 10, 2000 under the accession number VKPM B-7926 and then converted to an international deposit under the provisions of the Budapest Treaty on May 18, 2001.

*E. coli* strains 382 and 382ΔgshA are separately cultivated with shaking (220 rpm) at 37° C. for 18 hours in 3 mL of nutrient broth. Then, 0.3 mL of the obtained cultures are each inoculated into 2 mL of fermentation medium in 20×200-mm test tubes and cultivated at 32° C. for 48 hours on a rotary shaker (220 rpm).

After the cultivation, the amount of L-arginine which accumulates in the medium is determined by paper chromatography using a mobile phase consisting of n-butanol:acetic acid:water=4:1:1 (v/v). A solution of ninhydrin (2%) in acetone is used as a visualizing reagent. A spot containing L-arginine is cut out, L-arginine is eluted with 0.5% water solution of CdCl$_2$, and the amount of L-arginine is estimated spectrophotometrically at 540 nm.

The composition of the fermentation medium (g/L) is as follows:

| | |
|---|---|
| Glucose | 48.0 |
| (NH$_4$)$_2$SO$_4$ | 35.0 |
| KH$_2$PO$_4$ | 2.0 |
| MgSO$_4$•7H$_2$O | 1.0 |
| Thiamine-HCl | 0.0002 |
| Yeast extract | 1.0 |
| L-isoleucine | 0.1 |
| CaCO$_3$ | 5.0 |

Glucose and magnesium sulfate are sterilized separately. CaCO$_3$ is dry-heat sterilized at 180° C. for 2 h. The pH is adjusted to 7.0.

Example 5

Production of L-Citrulline by *E. coli* 382ΔargGΔgshA

To test the effect from inactivation of the gshA gene on L-citrulline production, the DNA-fragments from the chromosome of the above-described *E. coli* MG1655ΔgshA::Cm$^R$ strain are transferred to the citrulline-producing *E. coli* strain 382ΔargG by P1-transduction to obtain the strain *E. coli* 382ΔargGΔgshA. The strain 382ΔargG is obtained by deletion of argG gene on the chromosome of the arginine-producing E. coli strain 382 (VKPM B-7926, EP1170358 A1) by the method initially developed by Datsenko K. A. and Wanner B. L. called "λRed/ET-mediated integration" (Datsenko K. A. and Wanner B. L., Proc. Natl. Acad. Sci. USA, 2000, 97(12):6640-6645). According to this procedure, the PCR-primers, each of which is homologous to both a region adjacent to the argG gene and a region adjacent to the gene which confers antibiotic resistance in the template plasmid, are constructed. The plasmid pMW118-λattL-cat-λattR (WO05/010175) is used as the template in the PCR.

E. coli strains 382ΔargG and 382ΔargGΔgshA are separately cultivated with shaking at 37° C. for 18 hours in 3 mL of nutrient broth. Then, 0.3 mL of the obtained cultures are each inoculated into 2 mL of fermentation medium in 20×200-mm test tubes and cultivated at 32° C. for 48 hours on a rotary shaker.

After the cultivation, the amount of L-citrulline which accumulates in the medium is determined by paper chromatography using a mobile phase consisting of butan-1-ol: acetic acid:water=4:1:1 (v/v). A solution of ninhydrin (2%) in acetone is used as a visualizing reagent. A spot containing citrulline is cut out, L-citrulline is eluted with 0.5% water solution of $CdCl_2$, and the amount of L-citrulline is estimated spectrophotometrically at 540 nm.

The composition of the fermentation medium (g/L) is as follows:

| | |
|---|---|
| Glucose | 48.0 |
| $(NH_4)_2SO_4$ | 35.0 |
| $KH_2PO_4$ | 2.0 |
| $MgSO_4 \cdot 7H_2O$ | 1.0 |
| Thiamine-HCl | 0.0002 |
| Yeast extract | 1.0 |
| L-Isoleucine | 0.1 |
| L-Arginine | 0.1 |
| $CaCO_3$ | 5.0 |

Glucose and magnesium sulfate are sterilized separately. $CaCO_3$ is dry-heat sterilized at 180° C. for 2 h. The pH is adjusted to 7.0.

Example 6

Production of L-Cysteine by E. coli JM15(ydeD)ΔgshA

To test the effect from inactivation of the gshA gene on L-cysteine production, the DNA-fragments from the chromosome of the above-described E. coli MG1655ΔgshA::$Cm^R$ strain are transferred to the cysteine-producing E. coli strain JM15(ydeD) by P1-transduction to obtain the strain E. coli JM15(ydeD)ΔgshA. The strain JM15(ydeD) is a derivative of E. coli JM15 (U.S. Pat. No. 6,218,168 B1), which has been transformed with DNA containing the ydeD gene (U.S. Pat. No. 5,972,663). The ydeD gene encodes a membrane protein, and it is not involved in a biosynthetic pathway of any L-amino acid.

Fermentation conditions and procedure for evaluation of L-cysteine production were described in detail in Example 6 of U.S. Pat. No. 6,218,168 B1.

Example 7

Production of L-Glutamic Acid by E. coli VL334thrC$^+$ΔgshA

To test the effect from inactivation of the gshA gene on L-glutamic acid production, the DNA-fragments from the chromosome of the above-described E. coli MG1655ΔgshA::$Cm^R$ strain are transferred to the glutamate-producing E. coli strain VL334thrC$^+$ (EP1172433 A1) by P1-transduction to obtain the strain E. coli VL334thrC$^+$ΔgshA. The strain VL334thrC$^+$ was deposited in the Russian National Collection of Industrial Microorganisms (VKPM; FGUP GosNII Genetika, Russian Federation, 117545 Moscow, 1 Dorozhny proezd, 1) on Dec. 6, 2004 under the accession number VKPM B-8961 and then converted to an international deposit under the provisions of the Budapest Treaty on Dec. 8, 2004.

E. coli strains VL334thrC$^+$ and VL334thrC$^+$ΔgshA are separately cultivated for 18-24 hours at 37° C. on L-agar plates. Then, one loop of the cells is transferred into 20×200-mm test tubes containing 2 mL of fermentation medium. Cultivation is carried out at 30° C. for 3 days with shaking.

After the cultivation, the amount of L-glutamic acid which accumulates in the medium is determined by paper chromatography using a mobile phase consisting of butan-1-ol:acetic acid:water=4:1:1 (v/v) with subsequent staining by ninhydrin (1% solution in acetone), elution of L-glutamic acid in 50% ethanol with 0.5% $CdCl_2$ and further estimation of the amount of L-glutamic acid at 540 nm.

The composition of the fermentation medium (g/L) is as follows:

| | |
|---|---|
| Glucose | 60.0 |
| $(NH_4)_2SO_4$ | 25.0 |
| $KH_2PO_4$ | 2.0 |
| $MgSO_4 \cdot 7H_2O$ | 1.0 |
| Thiamine-HCl | 0.1 |
| L-Isoleucine | 0.07 |
| $CaCO_3$ | 25.0 |

Glucose and $CaCO_3$ are sterilized separately. The pH is adjusted to 7.2.

Example 8

Production of L-Histidine by E. coli MG1655+hisG$^r$ hisL'_Δ ΔpurR ΔgshA

To test the effect from inactivation of the gshA gene on L-histidine production, the DNA-fragments from the chromosome of the above-described E. coli MG1655ΔgshA::$Cm^R$ strain are transferred to the L-histidine-producing E. coli strain MG1655+hisG$^r$ hisL'_Δ ΔpurR using the P1-transduction to obtain the strain E. coli MG1655+hisG$^r$ hisL'_Δ ΔpurR ΔgshA. The strain MG1655+hisG$^r$ hisL'_Δ ΔpurR was described in RU2119536 C1 and Doroshenko V. G. et al., The directed modification of Escherichia coli MG1655 to obtain histidine-producing mutants, Prikl. Biochim. Mikrobiol. (Russian), 2013, 49(2):149-154.

E. coli strains MG1655+hisG$^r$ hisL'_Δ ΔpurR and MG1655+hisG$^r$ hisL'_Δ ΔpurR ΔgshA are separately cultivated for 3 hours at 30° C. in 2 mL of L-broth (Sambrook J. and Russell D. W., Molecular Cloning: A Laboratory Manual (3$^{rd}$ ed.), Cold Spring Harbor Laboratory Press, 2001). Then, 0.1 mL of the obtained cultures are each inoculated into 2 mL of fermentation medium in 20×200-mm test tubes and cultivated for 65 hours at 30° C. on a rotary shaker (250 rpm).

The composition of the fermentation medium (g/L) is as follows:

| | |
|---|---|
| Glucose | 50.0 |
| Mameno* | 0.2 (as the amount of nitrogen) |
| L-aspartate | 1.0 |
| $(NH_4)_2SO_4$ | 18.0 |
| KCl | 1.0 |
| $KH_2PO_4$ | 0.5 |
| $MgSO_4 \cdot 7H_2O$ | 0.4 |
| $FeSO_4 \cdot 7H_2O$ | 0.02 |
| $MnSO_4 \cdot 5H_2O$ | 0.02 |
| $ZnSO_4 \cdot 7H_2O$ | 0.02 |
| Adenosine | 0.2 |
| Thiamine-HCl | 0.001 |
| Betaine | 2.0 |
| $CaCO_3$ | 60.0 |

*Mameno is the soybean meal hydrolysate (Ajinomoto Co, Inc.).

Glucose, magnesium sulphate, betaine, and $CaCO_3$ are sterilized separately. The pH is adjusted to 6.0 by 6M KOH solution before sterilization.

After the cultivation, the amount of L-histidine which accumulates in the medium is determined by thin layer chromatography (TLC). The 10×15-cm TLC plates coated with 0.11-mm layers of Sorbfil silica gel containing non-fluorescent indicator (Stock Company Sorbpolymer, Krasnodar, Russian Federation) are used. The Sorbfil plates are developed with a mobile phase consisting of propan-2-ol: acetone:25% aqueous ammonia:water=6:6:1.5:1 (v/v). A solution of ninhydrin (2%, w/v) in acetone is used as a visualizing reagent. After development, plates are dried and scanned with the Camag TLC Scanner 3 in absorbance mode with detection at 520 nm using winCATS software (version 1.4.2).

Example 9

Production of L-Leucine by E. coli 57ΔgshA

To test the effect from inactivation of the gshA gene on L-leucine production, the DNA-fragments from the chromosome of the above-described E. coli MG1655ΔgshA::$Cm^R$ strain are transferred to the leucine-producing E. coli strain 57 (VKPM B-7386, U.S. Pat. No. 6,124,121) by P1-transduction to obtain the strain E. coli 57ΔgshA. The strain 57 was deposited in the Russian National Collection of Industrial Microorganisms (VKPM; FGUP GosNII Genetika, Russian Federation, 117545 Moscow, $1^{st}$ Dorozhny proezd, 1) on May 19, 1997 under the accession number VKPM B-7386.

E. coli strains 57 and 57ΔgshA are separately cultivated for 18-24 hours at 37° C. on L-agar plates. To obtain a seed culture, the strains are each grown on a rotary shaker (250 rpm) at 32° C. for 18 hours in 20×200-mm test tubes containing 2 mL of L-broth (Sambrook J. and Russell D. W., Molecular Cloning: A Laboratory Manual ($3^{rd}$ ed.), Cold Spring Harbor Laboratory Press, 2001) supplemented with sucrose (4%). Then, the fermentation medium is inoculated with 0.2 mL of seed culture (10%). The fermentation is performed in 2 mL of a minimal fermentation medium in 20×200-mm test tubes. Cells are grown for 48-72 hours at 32° C. with shaking at 250 rpm.

After the cultivation, the amount of L-leucine which accumulates in the medium is determined by paper chromatography using a mobile phase consisting of butan-1-ol: acetic acid:water=4:1:1 (v/v).

The composition of the fermentation medium (g/L) is as follows:

| | |
|---|---|
| Glucose | 60.0 |
| $(NH_4)_2SO_4$ | 25.0 |
| $K_2HPO_4$ | 2.0 |
| $MgSO_4 \cdot 7H_2O$ | 1.0 |
| Thiamine-HCl | 0.01 |
| $CaCO_3$ | 25.0 |

Glucose is sterilized separately. $CaCO_3$ is dry-heat sterilized at 180° C. for 2 h. The pH is adjusted to 7.2.

Example 10

Production of L-Lysine by E. coli AJ11442ΔgshA

To test the effect from inactivation of the gshA gene on L-lysine production, the DNA-fragments from the chromosome of the above-described E. coli MG1655ΔgshA::$Cm^R$ strain are transferred to the lysine-producing E. coli strain AJ11442 by P1-transduction to obtain the strain E. coli AJ11442ΔgshA. The strain AJ11442 was deposited in National Institute of Bioscience and Human Technology of Agency of Industrial Science and Technology (currently, NITE IPOD, #120, 2-5-8 Kazusakamatari, Kisarazu-shi, Chiba-ken, 292-0818, Japan) on May 1, 1981 under the accession number of FERM P-5084 and then converted to an international deposit under the provisions of the Budapest Treaty on Oct. 29, 1987 to be assigned an accession number of FERM BP-1543.

E. coli strains AJ11442 and AJ11442ΔgshA are separately cultivated in L-medium containing streptomycin (20 mg/L) at 37° C. Then, 0.3 mL of the obtained cultures are each inoculated into 20 mL of fermentation medium containing the required drugs in a 500-mL flask. The cultivation is carried out at 37° C. for 16 hours by using a reciprocal shaker at the agitation speed of 115 rpm.

After the cultivation, the amount of L-lysine which accumulates in the medium and residual glucose are determined by a known method (Biotech-analyzer AS210, Sakura Seiki Co.). Then, the yield of L-lysine is calculated relative to consumed glucose for each of the strains.

The composition of the fermentation medium (g/L) is as follows:

| | |
|---|---|
| Glucose | 40.0 |
| $(NH_4)_2SO_4$ | 24.0 |
| $K_2HPO_4$ | 1.0 |
| $MgSO_4 \cdot 7H_2O$ | 1.0 |
| $FeSO_4 \cdot 7H_2O$ | 0.01 |
| $MnSO_4 \cdot 5H_2O$ | 0.01 |
| Yeast extract | 2.0 |

The pH is adjusted to 7.0 by KOH, and the medium is autoclaved at 115° C. for 10 min. Glucose and magnesium sulfate are sterilized separately. $CaCO_3$ is dry-heat sterilized at 180° C. for 2 hours and added to the medium to a final concentration of 30 g/L.

Example 11

Production of L-Ornithine by E. coli 382ΔargFΔargI,ΔgshA

To test the effect from inactivation of the gshA gene on L-ornithine production, the DNA-fragments from the chromosome of the above-described *E. coli* MG1655ΔgshA::Cm$^R$ strain are transferred to the ornithine-producing *E. coli* strain 382ΔargFΔargI by P1-transduction to obtain the strain *E. coli* 382ΔargFΔargI,ΔgshA. The strain 382ΔargFΔargI is obtained by consecutive deletion of argF and argI genes on the chromosome of the arginine-producing *E. coli* strain 382 (VKPM B-7926, EP1170358 A1) by the method initially developed by Datsenko K. A. and Wanner B. L. called "λRed/ET-mediated integration" (Datsenko K. A. and Wanner B. L., *Proc. Natl. Acad. Sci. USA*, 2000, 97(12):6640-6645). According to this procedure, two pairs of PCR-primers homologous to both the region adjacent to the argF or argI gene and the gene which confers antibiotic resistance in the template plasmid are constructed. The plasmid pMW118-ΔattL-cat-ΔattR (WO05/010175) is used as the template in the PCR.

*E. coli* strains 382ΔargFΔargI and 382ΔargFΔargI,ΔgshA are separately cultivated with shaking at 37° C. for 18 hours in 3 mL of nutrient broth. Then, 0.3 mL of the obtained cultures are each inoculated into 2 mL of fermentation medium in 20×200-mm test tubes and cultivated at 32° C. for 48 hours on a rotary shaker.

After the cultivation, the amount of L-ornithine which accumulates in the medium is determined by paper chromatography using a mobile phase consisting of butan-1-ol:acetic acid:water=4:1:1 (v/v). A solution of ninhydrin (2%) in acetone is used as a visualizing reagent. A spot containing ornithine is cut out, ornithine is eluted with 0.5% water solution of CdCl$_2$, and the amount of ornithine is estimated spectrophotometrically at 540 nm.

The composition of the fermentation medium (g/L) is as follows:

| | |
|---|---|
| Glucose | 48.0 |
| (NH$_4$)$_2$SO$_4$ | 35.0 |
| KH$_2$PO$_4$ | 2.0 |
| MgSO$_4$•7H$_2$O | 1.0 |
| Thiamine-HCl | 0.0002 |
| Yeast extract | 1.0 |
| L-Isoleucine | 0.1 |
| L-Arginine | 0.1 |
| CaCO$_3$ | 5.0 |

Glucose and magnesium sulfate are sterilized separately. CaCO$_3$ is dry-heat sterilized at 180° C. for 2 h. The pH is adjusted to 7.0.

Example 12

Production of L-Phenylalanine by *E. coli* AJ12739ΔgshA

To test the effect from inactivation of the gshA gene on L-phenylalanine production, the DNA-fragments from the chromosome of the above-described *E. coli* MG1655ΔgshA::Cm$^R$ are transferred to the phenylalanine-producing *E. coli* strain AJ12739 by P1-transduction to obtain strain AJ12739ΔgshA. The strain AJ12739 was deposited in the Russian National Collection of Industrial Microorganisms (VKPM; FGUP GosNII Genetika, Russian Federation, 117545 Moscow, 1$^{st}$ Dorozhny proezd, 1) on Nov. 6, 2001 under the accession number VKPM B-8197 and then converted to an international deposit under the provisions of the Budapest Treaty on Aug. 23, 2002.

*E. coli* strains AJ12739 and AJ12739ΔgshA are separately cultivated at 37° C. for 18 hours in a nutrient broth. Then, 0.3 mL of the obtained cultures are each inoculated into 3 mL of fermentation medium in 20×200-mm test tubes and cultivated at 37° C. for 48 hours with shaking on a rotary shaker.

After the cultivation, the amount of L-phenylalanine which accumulates in the medium is determined by thin layer chromatography (TLC). The 10×15-cm TLC plates coated with 0.11-mm layers of Sorbfil silica gel containing non-fluorescent indicator (Stock Company Sorbpolymer, Krasnodar, Russian Federation) are used. The Sorbfil plates are developed with a mobile phase consisting of propan-2-ol:ethyl acetate:25% aqueous ammonia:water=40:40:7:16 (v/v). A solution of ninhydrin (2%) in acetone is used as a visualizing reagent.

The composition of the fermentation medium (g/L) is as follows:

| | |
|---|---|
| Glucose | 40.0 |
| (NH$_4$)$_2$SO$_4$ | 16.0 |
| K$_2$HPO$_4$ | 0.1 |
| MgSO$_4$•7H$_2$O | 1.0 |
| FeSO$_4$•7H$_2$O | 0.01 |
| MnSO$_4$•5H$_2$O | 0.01 |
| Thiamine-HCl | 0.0002 |
| Yeast extract | 2.0 |
| L-Tyrosine | 0.125 |
| CaCO$_3$ | 20.0 |

Glucose and magnesium sulfate are sterilized separately. CaCO$_3$ is dry-heat sterilized at 180° C. for 2 h. The pH is adjusted to 7.0.

Example 13

Production of L-Proline by *E. coli* 702ilvAΔgshA

To test the effect from inactivation of the gshA gene on L-proline production, the DNA-fragments from the chromosome of the above-described *E. coli* MG1655ΔgshA::Cm$^R$ strain are transferred to the proline-producing *E. coli* strain 702ilvA by P1-transduction to obtain the strain *E. coli* 702ilvAΔgshA. The strain 702ilvA was deposited in the Russian National Collection of Industrial Microorganisms (VKPM; FGUP GosNII Genetika, Russian Federation, 117545 Moscow, 1$^{st}$ Dorozhny proezd, 1) on Jul. 18, 2000 under the accession number VKPM B-8012 and then converted to an international deposit under the provisions of the Budapest Treaty on May 18, 2001.

*E. coli* strains 702ilvA and 702ilvAΔgshA are separately cultivated for 18-24 hours at 37° C. on L-agar plates. Then, these strains are each cultivated under the same conditions as in Example 7 (Production of L-glutamic acid).

Example 14

Production of L-Threonine by *E. coli* B-3996ΔgshA

To test the effect from inactivation of the gshA gene on L-threonine production, the DNA-fragments from the chromosome of the above-described *E. coli* MG1655ΔgshA::Cm$^R$ strain are transferred to the threonine-producing *E. coli* strain VKPM B-3996 by P1-transduction to obtain the strain B-3996ΔgshA. The strain VKPM B-3996 was deposited on Nov. 19, 1987 in the All-Union Scientific Center of Antibiotics (Russian Federation, 117105 Moscow, Nagatinskaya Street, 3-A) under the accession number RIA 1867. The strain was also deposited in the Russian National Collection of Industrial Microorganisms (VKPM; FGUP GosNII Genetika, Russian Federation, 117545 Moscow, 1st Dorozhny proezd, 1) on Dec. 19, 2002 under the accession number VKPM B-3996.

E. coli strains VKPM B-3996 and B-3996ΔgshA are separately cultivated for 18-24 hours at 37° C. on L-agar plates. To obtain a seed culture, the strains are each grown on a rotary shaker (250 rpm) at 32° C. for 18 hours in 20×200-mm test tubes containing 2 mL of L-broth (Sambrook J. and Russell D. W., Molecular Cloning: A Laboratory Manual (3rd ed.), Cold Spring Harbor Laboratory Press, 2001) supplemented with glucose (4%). Then, the fermentation medium is inoculated with 0.2 mL (10%) of seed culture. The fermentation is performed in 2 mL of minimal medium in 20×200-mm test tubes. Cells are grown for 65 hours at 32° C. with shaking at 250 rpm.

After the cultivation, the amount of L-threonine which accumulates in the medium is determined by paper chromatography using a mobile phase consisting of butan-1-ol: acetic acid:water=4:1:1 (v/v). A solution of ninhydrin (2%) in acetone is used as a visualizing reagent. A spot containing L-threonine is cut out, L-threonine is eluted with 0.5% water solution of $CdCl_2$, and the amount of L-threonine is estimated spectrophotometrically at 540 nm.

The composition of the fermentation medium (g/L) is as follows:

| | |
|---|---|
| Glucose | 80.0 |
| $(NH_4)_2SO_4$ | 22.0 |
| NaCl | 0.8 |
| $KH_2PO_4$ | 2.0 |
| $MgSO_4·7H_2O$ | 0.8 |
| $FeSO_4·7H_2O$ | 0.02 |
| $MnSO_4·5H_2O$ | 0.02 |
| Thiamine-HCl | 0.0002 |
| Yeast extract | 1.0 |
| $CaCO_3$ | 30.0 |

Glucose and magnesium sulfate are sterilized separately. $CaCO_3$ is sterilized by dry-heat at 180° C. for 2 h. The pH is adjusted to 7.0. The antibiotic is introduced into the medium after sterilization.

Example 15

Production of L-Tryptophan by E. coli SV164(pGH5)ΔgshA

To test the effect from inactivation of the gshA gene on L-tryptophan production, the DNA-fragments from the chromosome of the above-described E. coli MG1655ΔgshA::$Cm^R$ strain are transferred to the tryptophan-producing E. coli strain SV164(pGH5) by P1-transduction to obtain the strain E. coli SV164(pGH5)ΔgshA. The strain SV164(pGH5) is a strain obtained by introducing the plasmid pGH5 into the E. coli strain SV164. The strain SV164 (JP 3032013 B) has the trpE allele encoding anthranilate synthase free from feedback inhibition by tryptophan. The strain SV164 is a strain obtained by introducing a mutation into the trpE gene in the E. coli strain YMC9 (ATCC 33927). The strain YMC9 is available from the American Type Culture Collection (10801 University Boulevard, Manassas, Va. 20110, United States of America). The plasmid pGH5 harbors a mutant serA gene encoding phosphoglycerate dehydrogenase free from feedback inhibition by serine. The strain SV164(pGH5) was described in detail in U.S. Pat. No. 6,180,373 B1 or EP0662143 B1.

E. coli strains SV164(pGH5) and SV164(pGH5)ΔgshA are separately cultivated with shaking at 37° C. for 18 hours in 3 mL of nutrient broth supplemented with tetracycline (20 mg/L, marker of pGH5 plasmid). Then, 0.3 mL of the obtained cultures are each inoculated into 3 mL of a fermentation medium containing tetracycline (20 mg/L) in 20×200-mm test tubes, and cultivated at 37° C. for 48 hours on a rotary shaker at 250 rpm.

After the cultivation, the amount of L-tryptophan which accumulates in the medium is determined by TLC as described in Example 12 (Production of L-phenylalanine). The fermentation medium components are listed in Table 3, but should be sterilized in separate groups (A, B, C, D, E, F, G, and H), as shown, to avoid adverse interactions during sterilization.

TABLE 3

| Solutions | Component | Final concentration, g/L |
|---|---|---|
| A | $KH_2PO_4$ | 1.5 |
| | NaCl | 0.5 |
| | $(NH_4)_2SO_4$ | 1.5 |
| | L-Methionine | 0.05 |
| | L-Phenylalanine | 0.1 |
| | L-Tyrosine | 0.1 |
| | Mameno* (as the amount of nitrogen) | 0.07 |
| B | Glucose | 40.0 |
| | $MgSO_4·7H_2O$ | 0.3 |
| C | $CaCl_2$ | 0.011 |
| D | $FeSO_4·7H_2O$ | 0.075 |
| | Sodium citrate | 1.0 |
| E | $Na_2MoO_4·2H_2O$ | 0.00015 |
| | $H_3BO_3$ | 0.0025 |
| | $CoCl_2·6H_2O$ | 0.00007 |
| | $CuSO_4·5H_2O$ | 0.00025 |
| | $MnCl_2·4H_2O$ | 0.0016 |
| | $ZnSO_4·7H_2O$ | 0.0003 |
| F | Thiamine-HCl | 0.005 |
| G | $CaCO_3$ | 30.0 |
| H | Pyridoxine | 0.03 |

The pH of solution A is adjusted to 7.1 with $NH_4OH$.

*Mameno is the soybean meal hydrolysate (Ajinomoto Co., Inc.).

While the invention has been described in detail with reference to preferred embodiments thereof, it will be apparent to one skilled in the art that various changes can be made, and equivalents employed, without departing from the scope of the invention. All the cited references herein are incorporated by reference as a part of this application.

INDUSTRIAL APPLICABILITY

According to the present invention, production of L-amino acids such as branched-chain L-amino acids by a bacterium of the family Enterobacteriaceae can be improved.

The invention claimed is:

1. A method for producing an L-amino acid comprising:
   (i) cultivating an L-amino acid-producing bacterium of the family Enterobacteriaceae in a culture medium to produce the L-amino acid in the culture medium, the bacterium, or both; and
   (ii) collecting said L-amino acid from the culture medium, the bacterium, or both, wherein said bacterium has been modified to attenuate expression of a gshA gene, and wherein said L-amino acid is a branched-chain L-amino acid.

2. The method according to claim 1, wherein said bacterium belongs to the genus *Escherichia*.

3. The method according to claim 2, wherein said bacterium is *Escherichia coli*.

4. The method according to claim 1, wherein said bacterium belongs to the genus *Pantoea*.

5. The method according to claim 4, wherein said bacterium is *Pantoea ananatis*.

6. The method according to claim 1, wherein said expression of the gshA gene is attenuated by inactivation of the gshA gene.

7. The method according to claim 6, wherein said gshA gene is deleted.

8. The method according to claim 1, wherein said gshA gene is selected from the group consisting of:
   (A) a DNA comprising the nucleotide sequence of SEQ ID NO: 1;
   (B) a DNA comprising a variant nucleotide sequence of SEQ ID NO: 1 due to the degeneracy of the genetic code;
   (C) a DNA having an identity of not less than 60% with respect to the entire nucleotide sequence of SEQ ID NO: 1, and wherein said DNA encodes a protein having an activity of γ-glutamate-cysteine ligase;
   (D) a DNA encoding a protein comprising the amino acid sequence of SEQ ID NO: 2;
   (E) a DNA encoding a protein comprising the amino acid sequence of SEQ ID NO: 2, but which includes one or more mutations comprising substitution, deletion, insertion, or addition of one or several amino acid residues, and wherein said protein has the activity of γ-glutamate-cysteine ligase; and
   (F) a DNA encoding a protein having an identity of not less than 65% with respect to the entire amino acid sequence of SEQ ID NO: 2, wherein said protein has the activity of γ-glutamate-cysteine ligase.

9. The method according to claim 1, wherein said branched-chain L-amino acid is selected from the group consisting of L-isoleucine, L-leucine, and L-valine.

10. The method according to claim 9, wherein said L-amino acid is L-valine.

11. The method according to claim 1, wherein said bacterium is *Escherichia coli* and said gshA gene is deleted.

* * * * *